United States Patent [19]

Shanklin, Jr. et al.

[11] Patent Number: 4,500,529
[45] Date of Patent: Feb. 19, 1985

[54] METHOD OF TREATING CARDIAC DISORDERS WITH N-(ARYLOXYALKYL)-N'-(AMINOALKYL-)UREAS

[75] Inventors: James R. Shanklin, Jr.; Christopher P. Johnson, III, both of Richmond, Va.

[73] Assignee: A. H. Robins Company, Incorporated, Richmond, Va.

[21] Appl. No.: 492,534

[22] Filed: May 9, 1983

Related U.S. Application Data

[63] Continuation-in-part of Ser. No. 265,510, May 20, 1981, abandoned.

[51] Int. Cl.$^3$ .................... A61K 31/535; A61K 31/17
[52] U.S. Cl. ................................. 514/235; 514/587; 514/595; 514/253; 514/255; 514/318; 514/331; 514/332; 514/343; 514/357; 514/428; 514/821; 544/131; 544/160; 544/168; 544/360; 544/400; 546/193; 546/194; 546/206; 546/215; 546/217; 546/230; 546/231; 546/261; 546/281; 546/291; 548/567; 564/17; 564/56
[58] Field of Search ............... 424/263, 274, 267, 250, 424/248.52, 248.5, 322, 248.53, 248.54

[56] References Cited

FOREIGN PATENT DOCUMENTS 2801187 7/1978 Fed. Rep. of Germany .

OTHER PUBLICATIONS

Koelzer, P., et al., *Arzneim.-Forsch.*, 9, 113–120 (1959).
Conant, J., *The Chemistry of Carbon Compounds*, Macmillan, New York, 1939, p. 264.

*Primary Examiner*—Richard A. Schwartz

[57] ABSTRACT

N-(Aryloxyalkyl)-N'-(aminoalkyl)ureas and thioureas having the formula:

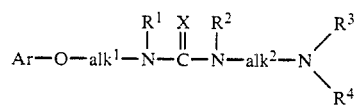

wherein $R^1$ and $R^2$ are hydrogen, loweralkyl, cycloalkyl, phenyl or phenyllower alkyl, and $R^3$ and $R^4$ are hydrogen, loweralkyl, phenyl and phenylalkyl or $R^3$ and $R^4$ taken together with the adjacent nitrogen form a heterocyclic residue are disclosed in a method of suppressing cardiac arrhythmias.

65 Claims, No Drawings

METHOD OF TREATING CARDIAC DISORDERS WITH N-(ARYLOXYALKYL)-N'-(AMINOALKYL)UREAS

This is a continuation-in-part application of application Ser. No. 265,510 filed May 20, 1981, now abandoned.

BACKGROUND OF THE INVENTION

1. Field of Invention

The present invention relates to N-(aryloxyalkyl)-N'-(aminoalkyl)ureas and thioureas, their acid addition salts and hydrates thereof and is particularly concerned with a process for administering the same to a living animal body for its cardiac antiarrhythmic effect and pharmaceutical methods and compositions associated therewith.

2. Description of the Prior Art

Procainamide hydrochloride which has the formula $NH_2C_6H_4—CONH—CH_2CH_2—N—(C_2H_5)_2 \cdot HCl$ has been used in the art to suppress certain cardiac arrhythmias.

Recently, Protiva, M. et al. have disclosed in Czech Patent 146,873 [C.A. 79, 42205g] compounds such as $ClC_6H_4—O(CH_2)_3—CO—NH(CH_2)_2—N—(C_2H_5)_2$ useful for lowering blood sugar levels in rats.

Joullie, M. et al. in Ger. Offen, 2,801,187 also have disclosed trimethoxyphenoxy carbamoyl compounds of the general structure $$(CH_3O)_3C_6H_2—X—(CH_2)_m—Y—(CH_2)_n—NR_1,R_2$$

wherein X is O or $NR_3$ and Y is CONH, $R_3$ is hydrogen, benzyl or morpholinoethyl, m and n are 0, 1 and 2. Some of the compounds disclosed are ureas but they are never urea at the same time X is O, i.e. phenoxy. Use of the compounds as tranquilizers, sedatives, muscle relaxants and spasmolytics is disclosed.

Koelzer, P. P. and Wehr, K. H. in Arzneim. Forsch 9, 113–20 (1959) disclosed two unsubstituted phenoxy compounds which fall within the scope of compounds useful in the pharmaceutical method of the present invention; namely, N'-[2-(Diethylamino)ethyl]-N-methyl-N-[2-(phenoxy)ethyl]urea and N-Methyl-N-[2-(phenoxy)ethyl]-N'-[2-(pyrrolidinyl)ethyl]urea Anesthetic activity in animals was disclosed but clinical use of these ureas was said to be unlikely. There is no disclosure of thiourea compounds.

OBJECTS AND SUMMARY OF THE INVENTION

The present invention is concerned with a novel method of treating cardiac arrhythmias in an animal which comprises administering to an animal in need thereof an N-(aryloxyalkyl)-N'-(aminoalkyl)urea having the following structure formula:

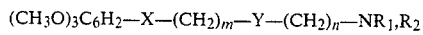

Formula I wherein;

Ar is 1 and 2-naphthyl, 2,3-dihydro-1H-inden-4(or 5)-yl, 3-pyridinyl, phenyl or phenyl substituted by 1–3 radicals which may be the same or different selected from the group consisting of loweralkyl, loweralkoxy, halogen, trifluoromethyl, amino, cyano, aminocarbonyl, nitro, loweralkylthio, loweralkylsulfinyl, loweralkylsulfonyl, loweralkanoyl, benzoylamino or loweralkanoylamino, $R^1$ and $R^2$ are selected from the group consisting of hydrogen, loweralkyl, cycloalkyl, phenyl, phenyl substituted by halogen, loweralkyl or loweralkoxy, or phenyl-loweralkyl wherein phenyl may be substituted by halogen, loweralkyl and lower alkoxy, X is selected from oxygen or sulfur, $R^3$ and $R^4$ are selected from the group consisting of hydrogen, loweralkyl, phenyl, phenyl substituted by halogen, loweralkyl or loweralkoxy, and phenyl-loweralkyl wherein phenyl may be substituted by halogen, loweralkyl and lower alkoxy, and $R^3$ and $R^4$ may be the same or different or taken together with the adjacent nitrogen form a heterocyclic residue, $alk^1$ and $alk^2$ are selected from the group consisting of loweralkylene or loweralkylene-loweralkyl and may be the same or different, and the pharmaceutically acceptable addition salts and hydrates thereof.

In the further definition of symbols in the formulas hereof and where they appear elsewhere throughout this specification and claims, the terms have the following significance.

The term "loweralkyl" as used herein includes straight and branched chain radicals of up to eight carbons inclusive and is exemplified by such groups as methyl, ethyl, propyl, isopropyl, butyl, sec. butyl, tert-butyl, amyl, isoamyl, hexyl, heptyl, and octyl radicals and the like. The term "loweralkoxy" has the formula —O—loweralkyl.

The term "cycloalkyl" as used herein includes primarily cyclic alkyl radicals containing 3 to 9 carbon atoms inclusive and includes such groups as cyclopropyl, cyclobutyl, cyclopentyl, cyclohexyl, methylcyclohexyl, cycloheptyl and the like.

The term "halogen" when referred to herein includes fluorine, chlorine, bromine and iodine, preferably fluorine, chlorine and bromine.

The term "loweralkylene" as used herein refers to connecting hydrocarbon groups represented by methylene (—$CH_2$—), ethylene (—$CH_2$—$CH_2$—), propylene (—$CH_2CH_2CH_2$—), and the like. The term "loweralkylene-loweralkyl" is represented by hydrocarbon groups such as

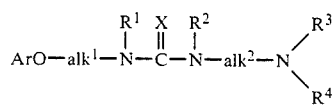

1,3-butylene [—CH—$CH_2$—$CH_2$—], and the like.
                    |
                    $CH_3$ The term "heterocyclic residue" as used herein refers to pyrrolidino, piperidino, 4-phenylpiperidino, 2,6-loweralkylpiperidino, 4-hydroxy-4-phenylpiperidino, 4-cyano-4-phenylpiperidino, 4-phenyl-1,2,3,6-tetrahydropyridino, piperazino, 4-loweralkylpiperazino, 4-phenylpiperazino, (4-phenyl-loweralkyl)-piperazino, or morpholino radicals.

"Pharmaceutically acceptable acid addition salts" are those salts formed by the N-(aryloxyalkyl)-N'-(aminoalkyl)ureas of this invention with any acid which is physiologically compatible in warm blooded animals, such salts being formed by either strong or weak acids. Representative of strong acids are hydrochloric, sulfuric and phosphoric acids. Representative of weak acids fumaric, maleic, succinic, tartaric, oxalic, citric, cyclohexamic and the like.

The compounds of the present invention exhibit antiarrhythmic activity in dogs, several arrhythmia models in which arrhythmia is induced by one or more of the following as described more fully hereinbelow under pharmacology: (1) Ouabain, (2) Ligation, (3) Injury, and (4) acetylcholine.

It is therefore an object of the present invention to provide methods and compositions for treating cardiac arrhythmias in living animal bodies utilizing certain N-(aryloxyalkyl)-N'-(aminoalkyl)ureas (and aminoalkylthioureas).

Another object of the invention is to provide certain novel N-(aryloxyalkyl)-N'-(aminoalkyl)ureas (and thioureas), salts and hydrates thereof and methods of making the same which have a high degree of cardiological activity.

Additional objects will be apparent to one skilled in the art and still other objects will become apparent hereinafter.

DETAILED DESCRIPTION OF THE INVENTION

The method of treating arrhythmias in living animals comprises administering N-(aryloxyalkyl)-N'-(aminoalkyl)ureas and thioureas and derivatives thereof as set forth hereinabove in Formula I and definitions therewith and as pharmaceutical compositions to a living animal body for cardiac arrhythmic effect in an amount effective to control arrhythmia.

The compounds of Formula I wherein X=oxygen are prepared by one of 4 methods, A, B, C or D. Compounds wherein X=sulfur are prepared by method A or D starting with thiophosgene.

Method A—This method is represented by the following equation:

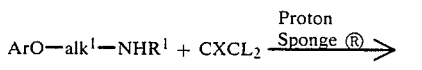

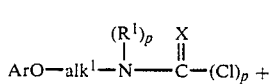

Intermediate III

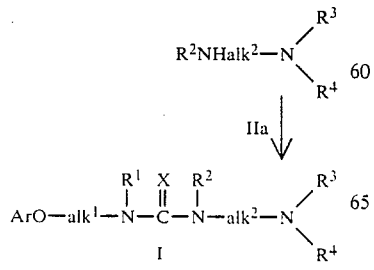

wherein; Ar, $R^1$, $R^2$, $R^3$, $R^4$ and $alk^1$ and $alk^2$ are as defined hereinabove and when $R^1$ is hydrogen, p is zero and the dotted line is a double bond forming an isocyanate; otherwise p is 1 and the dotted line has no significance; with the proviso that when $R^2$ is not hydrogen, $R^3$ and $R^4$ must be other than hydrogen, or $R^2$ is the same as $R^3$, and $R^4$ is hydrogen.

Generally, in Method A the aryloxyalkyl amine is reacted with phosgene (or thiophosgene) in a suitable organic solvent plus Proton Sponge ®, which is 1,8-bis-(dimethylamino) naphthalene followed by extraction (washing) with dilute sulfuric acid and the organic layer is dried and evaporated to an oil (Intermediate, Formula III) which may, if desired, be isolated as in Example 46 and later used as in Example 3A. The oil is dissolved in tetrahydrofuran and reacted with an amine of Formula IIa. The reaction mixture is stripped to dryness and the residue partitioned between water and a solvent such as methylene chloride. Evaporation of the solvent yields an oil which may or may not crystallize. Pharmaceutically acceptable salts may be prepared by reacting with an appropriate acid. The method is illustrated more specifically in Examples 1, 2, 3 and other examples wherein aryloxyamines are reacted with phosgene or thio phosgene.

Method B—This method is represented by the following equation:

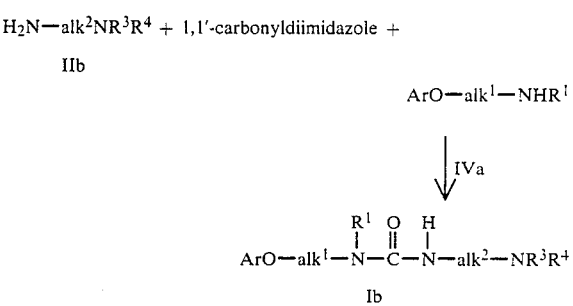

wherein Ar, $R^1$, $R^3$, $R^4$, $alk^1$ and $alk^2$ are as defined hereinabove. Formula Ib is encompassed by Formula I and $R^2$ is always hydrogen in this method.

Generally, in Method B an alkyldiamine is reacted first with 1,1'-carbonyldiimidazole in a suitable solvent (e.g., tetrahydrofuran) followed by reaction with a solution of the aryloxy-alkylamine. The reaction mixture is quenched in water and extracted with a suitable solvent (e.g., methylene chloride) or the reaction mixture is evaporated to dryness and the residue partitioned between water and a suitable organic solvent. The organic layer in either case is dried and evaporated to yield an oil, the free base. Pharmaceutically acceptable acid addition salts may then be provided with a suitable acid. The method is illustrated more fully in Example 18.

Method C—This method is represented by the following equation:

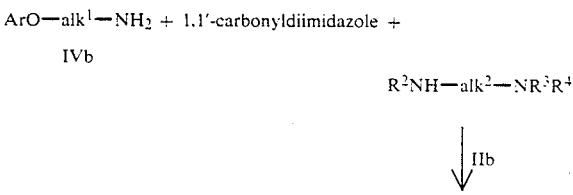

-continued $$ArO-alk^1-\overset{H}{\underset{|}{N}}-\overset{O}{\underset{||}{C}}-\overset{R^2}{\underset{|}{N}}-alk^2-N\diagdown\overset{R^3}{\underset{R^4}{}}$$
Ic wherein Ar, $R^2$, $R^3$, $R^4$, $alk^1$ and $alk^2$ are as defined hereinabove and $R^1$ is always hydrogen in this method. Formula Ic is encompassed by Formula I.

Generally, in Method C aryloxyalkyl amine is reacted first with 1,1'-carbonyldiimidazole in a suitable solvent (e.g., tetrahydrofuran) followed by reaction with an alkyldiamine having one free hydrogen. The solvent is removed by evaporation and the residue partitioned between a suitable solvent (e.g., chloroform) and water. The free base is obtained by evaporation and may be converted to a pharmaceutically acceptable salt with a suitable acid. The method is illustrated more fully in Example 33.

Method D—This method is represented by the following equation:

$$\overset{R^3}{\underset{R^4}{\diagdown}}N-alk^2-NHR^2 + CXCl_2 \longrightarrow$$
IIa $$\overset{R^3}{\underset{R^4}{\diagdown}}N-alk^2-\overset{R^2}{\underset{|}{N}}-\overset{X}{\underset{||}{C}}-Cl$$
Intermed. V triethylamine $\big|$ + $Ar-O-alk^1-NHR^1$
IVa $$ArO-alk^1-\overset{R^1}{\underset{|}{N}}-\overset{X}{\underset{||}{C}}-\overset{R^2}{\underset{|}{N}}-alk^2-N\diagdown\overset{R^3}{\underset{R^4}{}}$$
Id wherein; Ar, $alk^1$, $alk^2$, $R^1$ and $R^2$ have the values assigned above except $R^2$, $R^3$ and $R^4$ are never hydrogen. Formula Id is encompassed by Formula I. See Example 52 for a demonstration of Method D.

Compounds wherein aryl is phenyl substituted by amino are obtained by catalytic hydrogenation of the corresponding nitro derivative; for example, over palladium-on-charcoal.

Starting compounds of Formula IVa are prepared by reacting aryloxyalkyl halides and the appropriate amine. Starting compounds of Formula IVb are prepared by reacting the aryloxyalkyl halide with potassium phthalimide followed by reaction with hydrazine hydrate. Starting compounds of Formula IIa and IIb are commercially available or may be prepared from the appropriate aminoalkyl chloride and potassium phthalimide followed by reaction with hydrazine hydrate. Preparations 1 to 56 more fully illustrate the preparation of starting compounds.

Preparation 1

2-(3,4-Dichlorophenoxy)-N-(1-methylethyl)ethanamine, Hydrochloride

A solution of 36.18 g. (0.135 mole) of 2-bromoethyl-3,4-dichlorophenyl ether and 31.8 g (0.54 mole) of isopropyl amine in 200 ml of chloroform was heated at reflux for 72 hours. Solvent was removed in a rotary evaporator and the residue partitioned between water and chloroform. The chloroform layer was extracted with 1N sulfuric acid. The aqueous phase, which contained a dispersed white solid, was made alkaline with 10% aqueous sodium hydroxide solution and extracted with chloroform. The chloroform layer was concentrated under vacuum to an oil, the free base. A portion of the oil was dissolved in methanol and treated with ethereal hydrogen chloride. The precipitate was recrystallized from methanol-diethyl ether. Overall yield of white crystalline product was 62.4% of theory based on the proportion taken. The melting point was 186°–187° C.

Analysis: Calculated for $C_{11}H_{15}NOCl_3$: C, 46.42; H, 5.67; N, 4.92, Found: C, 46.53; H, 5.69; N, 5.00.

Preparation 2

2-(3,5-Dichlorophenoxy)-N-(1-methylethyl)ethanamine, Hydrochloride

Following the procedure of Preparation 1, 2-bromoethyl-3,5-dichlorophenyl ether and isopropyl amine were reacted in refluxing chloroform overnight) to yield an oil, the free base of the title compound. Thereafter, a portion of the oil was reacted with ethereal hydrogen chloride to form the hydrochloride salt in 43.4% yield, m.p. 195°–197° C.

Analysis: Calculated for $C_{11}H_{16}NOCl_3$: C, 46.42; H, 5.67; N, 4.92, Found: C, 46.38; H, 5.64; N, 4.95.

Preparation 3

3-(3,5-Dichlorophenoxy)-N-(1-methylethyl)-1-propanamine, Hydrochloride

Following the procedure of Preparation 1, a mixture of 3-[3,5-dichlorophenoxy]-1-chloropropane and 3-[3,5-dichlorophenoxy]-1-bromopropane and isopropyl amine were reacted in refluxing chloroform overnight and the reaction mixture processed to yield an oil, the free base of the title compound. A portion of the oil was reacted with ethereal hydrogen chloride to form the hydrochloride salt; m.p. 157°–159° C.

Analysis: Calculated for $C_{12}H_{18}NOCl_3$: C, 48.26; H, 6.08; N, 4.69, Found: C, 48.29; H, 6.03; N, 4.76.

Preparation 4

N-(1-Methylethyl)-2-phenoxyethanamine, Hydrochloride

Following the procedure of Preparation 1, 2-bromoethyl phenyl ether and isopropyl amine were reacted (in refluxing chloroform) overnight and the reaction mixture processed to yield an oil, the free base of the title compound. A portion of the oil was reacted with ethereal hydrogen chloride to form the hydrochloride salt in 68.3% yield, m.p. 152°–154.5° C.

Analysis: Calculated for $C_{11}H_{18}NOCl$: C, 61.25; H, 8.41; N, 6.49, Found: C, 61.50; H, 8.50; N, 6.53.

Preparation 5

2-[2-[[N,N-bis(1-Methylethyl)]amino]ethyl]-2H-isoindole-1,3-dione, Hydrochloride A solution of 40.0 g (0.2 mole) of 2-diisopropylaminoethyl chloride hydrochloride and 74.0 g (0.4 mole) of potassium phthalimide in 500 ml of dimethylformamide were stirred overnight at 85° C. The reaction mixture was stripped to dryness on a rotary evaporator under reduced pressure, and the residue was partitioned between chloroform and water. The chloroform layer was extracted with 10% aqueous sodium hydroxide, dried over sodium sulfate and stripped to yield a brown oil, the free base of the title compound which slowly crystallized. A portion of the oil was reacted with ethereal hydrogen chloride to form the hydrochloride salt, which was recrystallized from methanol-diethyl ether, in 62.3% yield, m.p. 209°–211° C.

Analysis: Calculated for $C_{16}H_{23}N_2O_2Cl$: C, 61.83; H, 7.46; N, 9.01, Found: C, 61.52; H, 7.42; N, 8.93.

Preparation 6

N,N-bis(1-Methylethyl)-1,2-ethanediamine, Dihydrochloride

A solution of 40.54 g (0.148 mole) of 2-[2-[[N,N-bis(1-methylethyl)]amino]ethyl]-2H-isoindole-1,3-dione (oil in Preparation 5 and 11.8 g (0.2 mole) of 85% hydrazine hydrate in 400 ml of 95% ethyl alcohol was heated at reflux for 5 hr. The reaction mixture was allowed to cool to room temperature while standing overnight during which time a white solid precipitated. The reaction mixture was concentrated nearly to dryness in a rotary evaporator. The residue was dissolved in chloroform and extracted with 10% aqueous sodium hydroxide solution. Evaporation of the chloroform layer gave a brown oil, the free base of the title compound. A portion of the oil was reacted with ethereal hydrogen chloride to form the hydrochloride salt which was recrystallized from methanol-diethyl ether. Yield was 20% of theory, m.p. 178°–182° C. (d).

Analysis: Calculated for $C_8H_{22}N_2Cl_2$: C, 44.24; H, 10.21; N, 12.90, Found: C, 43.93; H, 10.15; N, 12.83.

Preparation 7

N-[2-(3,4-Dimethoxyphenoxy)ethyl]-1-methylethanamine, Hydrochloride

A solution of 17.06 g (0.068 mole) of 2-bromoethyl 3,4-dimethoxyphenyl ether in 500 ml of isopropyl amine was stirred overnight at room temperature. The reaction mixture was stripped to dryness and the residue partitioned between water and chloroform. The chloroform layer was then extracted with 10% sodium hydroxide. The organic layer was then extracted with 1N sulfuric acid. The acidic layer was then made alkaline and extracted with chloroform. Removal of chloroform gave a brown oil, the free base of the title compound. Three grams of the oil was converted to the hydrochloride salt and recrystallized from methanol-diethylether. White crystalline product 2.67 g (58.5%), m.p. 139°–141° C. after drying overnight in vacuo at 100° C. was obtained.

Analysis: Calculated for $C_{13}H_{22}NO_3Cl$: C, 56.62; H, 8.04; N, 5.08, Found: C, 56.53; H, 8.06; N, 5.10.

Preparation 8

N-[2-(2,4-Dichlorophenoxy)ethyl]-1-methylethanamine, Maleate [1:1]

1-Bromo-2-(2,4-dichlorophenoxy)ethane, 72.22 g (0.27 mole), and isopropyl amine in excess as solvent were reacted at room temperature with stirring for 18 hr and the reaction mixture processed to yield a solid, the free base of the title compound. A portion of the solid was reacted with maleic acid and recrystallized from methanol-methylene chloride-diethyl ether to yield a white crystalline solid, m.p. 143°–145° C.

Analysis: Calculated for $C_{15}H_{19}NO_5Cl_2$: C, 49.47; H, 5.26; N, 3.85, Found: C, 49.37; H, 5.22; N, 3.88.

Preparation 9

N-[2-(3,5-Dichlorophenoxy)ethyl]benzeneamine, Hydrochloride

A solution of 16.08 g (0.06 mole) 3,5-dichlorophenyl-2-bromoethyl ether in 100 ml aniline (excess) was stirred overnight at room temperature. The unreacted aniline was removed in a rotary evaporator with vacuum distillation. The residue was triturated with isopropyl ether and chilled in a methanol-dry ice bath. A purple solid aniline hydrobromide was filtered from the mixture and discarded. The filtrate was evaporated to dryness yielding 15.25 g of oil, the free base of the title compound. A portion of the oil was reacted with ethereal hydrogen chloride to form the hydrochloride salt which was recrystallized from methanol-diethyl ether in 40.0% overall yield, m.p. 193°–196° C.

Analysis: Calculated for $C_{14}H_{14}NOCl_3$: C, 52.77; H, 4.43; N, 4.40, Found: C, 52.79; H, 4.39; N, 4.59.

Preparation 10

1-(2-Bromoethoxy)naphthalene

A solution of 144.0 g (1 mole) α-naphthol and 56.1 g (1 mole) potassium hydroxide in 600 ml of 95% ethanol was stirred 1.5 hr at room temperature. To this solution of potassium naphthalate was added 930.0 g (5.0 mole) of 1,2-dibromoethane, and the solution was heated at reflux overnight. The reaction mixture was filtered, and the filtrate stripped to dryness under reduced pressure in a rotary evaporator. The resulting oil was dissolved in chloroform and the solution extracted with 10% aqueous sodium hydroxide. The chloroform layer was dried and stripped of chloroform to yield 126 g (50.3%) of dark brown oil.

Preparation 11

1-Methyl-N-[2-(1-naphthalenyloxy)ethyl]ethanamine Hydrochloride

A solution of 25.0 g (0.1 mole) of 2-bromoethyl-α-naphthyl ether and 100 ml of isopropyl amine (excess) was stirred at room temperature overnight. The reaction mixture was stripped to dryness and partitioned between chloroform and water. Evaporation of the chloroform layer gave an oil, the free base of the title compound. A portion of the oil was reacted with ethereal hydrogen chloride and the hydrochloride salt recrystallized from methanol-diethyl ether. Overall yield was 89.3%, m.p. 198°–200° C.

Analysis: Calculated for $C_{15}H_{20}NOCl$: C, 67.79; H, 7.56; N, 5.27, Found: C, 67.75; H, 7.61; N, 5.24.

Preparation 12

N-[2-(3-Chlorophenoxy)ethyl]-1-methylethanamine, Hydrochloride

Following the procedure of Preparation 11, 2-bromoethyl-3-chlorophenyl ether and isopropyl amine in excess were reacted and the reaction mixture processed to yield an oil, the free base of the title compound. A portion of the oil converted to the hydrochloride salt (77.8%), m.p. 153.5°–155.5° C.

Analysis: Calculated for $C_{11}H_{17}NOCl_2$: C, 52.81; H, 6.85; N, 5.60, Found: C, 52.83; H, 6.89; N, 5.69.

Preparation 13

N-[2-(2,6-Dichlorophenoxy)ethyl]-1-methylethanamine, Maleate

Following the procedure of Preparation 11, 30.0 g (0.112 mole) of 2-bromoethyl-2,6-dichlorophenyl ether and isopropyl amine in excess were reacted and the reaction mixture processed to yield an oil, the free base of the title compound. A portion of the oil was converted to the maleate salt, m.p. 143°–144° C.

Analysis: Calculated for $C_{15}H_{19}NO_5Cl_2$: C, 49.46; H, 5.26; N, 3.84, Found: C, 49.55; H, 5.30; N, 3.84.

Preparation 14

2-[2-(3,5-Dichlorophenoxy)ethyl]-1H-isoindole-1,3(2H)-dione

A mixture of 101.88 g (0.38 mole) of 2-bromoethyl-3,5-dichlorophenyl ether and 70.3 g (0.38 mole) of potassium phthalimide in 800 ml of dimethylformamide was stirred overnight at 85° C. The reaction mixture was filtered and dimethylformamide removed from the filtrate in a rotary evaporator to yield a white solid. The solid was triturated with diethyl ether and the mixture filtered. The solid was dried in vacuo. Recrystallized from methylene chloride-hexane, the product melted at 133+–136° C. Yield overall was 41.7%.

Analysis: Calculated for $C_{16}H_{11}NO_3Cl_2$: C, 57.17; H, 3.30; N, 4.17, Found: C, 57.04; H, 3.29; N, 4.15.

Preparation 15

2-(3,5-Dichlorophenoxy)ethanamine, Hydrochloride

A mixture of 105.5 g (0.31 mole) of 2-[2-(3,5-dichlorophenoxy)ethyl]-1H-isoindole-1,3-(2H)-dione and 24.5 g (0.41 mole) 85% hydrazine hydrate in 1 liter of 95% ethanol was heated at reflux for 4 hr. A white solid was filtered off and discarded. The filtrate was stripped to dryness and the residue partitioned between water and chloroform. The chloroform layer was washed with aqueous 10% sodium hydroxide solution and then extracted with 1N sulfuric acid. The aqueous acidic layer was made alkaline and extracted with chloroform. The chloroform layer was dried over magnesium sulfate and evaporated to obtain an oil, the free base of the title compound. A portion of the oil was reacted with ethereal hydrogen chloride to give white crystalline product in 43.2% yield, m.p. 229°–231° C.

Analysis: Calculated for $C_8H_{10}NOCl_3$: C, 39.62; H, 4.16; N, 5.78, Found: C, 39.22; H, 4.11; N, 5.86.

Preparation 16

N-(1-Methylethyl)-2-(3,5-dimethylphenoxy)ethanamine, Maleate

A solution of 36.2 g (0.159 mole) of 1-bromo-2-(3,5-dimethylphenoxy)ethane in 400 ml of isopropyl amine (excess) was stirred at room temperature for 20 hr. The reaction mixture was quenched in a large excess of dilute aqueous sodium hydroxide solution and the mixture extracted with methylene chloride. The methylene chloride extract was washed several times with dilute aqueous sodium hydroxide solution and dried over magnesium sulfate. The methylene chloride was removed in vacuo to give an oil, the free base of the title compound, in an amount of 28.3 g. A small portion of the oil was reacted with maleic acid and recrystallized from methanol-diethyl ether to give a white crystalline solid, m.p. 158°–159.5° C.

Analysis: Calculated for $C_{17}H_{25}NO_5$: C, 63.14; H, 7.79; N, 4.33, Found: C, 63.14; H, 7.80; N, 4.32.

Preparation 17

N-(1-Methylethyl)-2-(3,5-dimethoxyphenoxy)ethanamine, Maleate

Following the procedure of Preparation 16, 1-bromo-2-(3,5-dimethoxyphenoxy)ethane and excess isopropyl amine were reacted and the reaction mixture processed to give an oil, the free base of the title compound. A portion of the oil was reacted with maleic acid. The white crystalline solid melted 128°–129.5° C.

Analysis: Calculated for $C_{17}H_{25}NO_7$: C, 57.45; H, 7.09; N, 3.94, Found: C, 57.35; H, 7.14; N, 3.97.

Preparation 18

N-[2-(3,4-Dimethylphenoxy)ethyl]-1-methylethanamine, Hydrochloride

Following the procedure of Preparation 16, 1-bromo-2-(3,4-dimethylphenoxy)ethane and excess isopropyl amine were reacted and the reaction mixture processed to give an oil, the free base of the title compound. A portion of the oil was reacted with ethereal hydrogen chloride. The white crystalline solid melted 148–149.5.

Analysis: Calculated for $C_{13}H_{22}NOCl$: C, 64.05; H, 9.10; N, 5.75, Found: C, 64.13; H, 9.18; N, 5.86.

Preparation 19

N-[2-(4-Chlorophenoxy)ethyl]-1-methylethanamine, Hydrochloride

Following the procedure of Preparation 11, 2-bromoethyl-4-chlorophenyl ether and isopropyl amine (excess) were reacted and the reaction mixture processed to give an oil, the free base of the title compound. A portion of the oil was reacted with ethereal hydrogen chloride to give the hydrochloride salt, m.p. 162°–164° C. in 69.3% yield.

Analysis: Calculated for $C_{11}H_{17}NOCl_2$: C, 52.81; H, 6.85; N, 5.60, Found: C, 52.72; H, 6.88; N, 5.71.

Preparation 20

N-[2-(2,5-Dichlorophenoxy)ethyl]-1-methylethanamine Hydrochloride

Following the procedure of Preparation 11, 2-bromoethyl-2,5-dichlorophenyl ether and isopropyl amine (excess) were reacted and the reaction mixture processed to give an oil, the free base of the title compound. A portion of the oil was reacted with ethereal hydrogen chloride to give the hydrochloride salt, m.p. 152°–155° C. in 63.3% yield.

Analysis: Calculated for $C_{11}H_{16}NOCl_3$: C, 46.42; H, 5.67; N, 4.92, Found: C, 46.39; H, 5.67; N, 4.94.

Preparation 21

1-Methyl-N-[2-(3-trifluoromethylphenoxy)ethyl]ethanamine Maleate

Following the procedure of Preparation 16, 1-bromo-2-(3-trifluoromethylphenoxy)ethane and isopropylamine were reacted and the reaction mixture processed to give an oil, the free base and the title compound. A portion of the oil was reacted with maleic acid to give the maleate salt, m.p. 125.5°–126.5° C.

Analysis: Calculated for $C_{16}H_{20}NO_5F$: C, 52.89; H, 5.55; N, 3.86, Found: C, 52.79; H, 5.57; N, 3.83.

Preparation 22

2-(3,5-Dichlorophenoxy)-N-methylethanamine, Hydrochloride

A solution of 31.56 g (0.118 mole) 2-bromoethyl-3,5-dichlorophenyl ether in excess methylamine was agitated overnight in a bomb at room temperature. The methylamine was evaporated under nitrogen and the residue partitioned between water and methylene chloride. The methylene chloride was evaporated to give an oil, the free base of the title compound. A portion of the oil was reacted with ethereal hydrogen chloride to give the hydrochloride salt which was recrystallized from methanol-diethyl ether to give a white crystalline product in 35.7% overall yield, m.p. 173°–175° C.

Analysis: Calculated for $C_9H_{12}NOCl_3$: C, 42.13; H, 4.72; N, 5.46, Found: C, 42.01; H, 4.69; N, 5.59.

Preparation 23

N-[2-(3-Fluorophenoxy)ethyl]-1-methylethanamine, Maleate

A solution of 20.94 g (0.096 mole) of 1-bromo-2-(3-fluorophenoxy)ethane in 300 ml of isopropylamine was stirred at room temperature overnight. The excess amine was removed in vacuo to give an oil (15.29 g), the free base of the title compound. A portion of the oil was reacted with maleic acid to give the maleate salt which was recrystallized from methanol-diethyl ether, m.p. 141°–142° C.

Analysis: Calculated for $C_{15}H_{20}NO_5F$: C, 57.50; H, 6.43; N, 4.47, Found: C, 57.51; H, 6.48; N, 4.44.

Preparation 24

N-[2-(2,3-Dichlorophenoxy)ethyl]-1-methylethanamine, Hydrochloride

Following the procedure of Example 11, 2-bromoethyl-2,3-dichlorophenyl ether was reacted with isopropyl amine (excess) and the reaction mixture processed to give an oil, the free base of the title compound. A portion of the oil was reacted with ethereal hydrogen chloride salt, m.p. 161°–163.5° C. in 62.7% yield.

Analysis: Calculated for $C_{11}H_{16}NOCl_3$: C, 46.42; H, 5.67; N, 4.92, Found: C, 46.23; H, 5.69; N, 5.02.

Preparation 25

N-[2-(2-Chlorophenoxy)ethyl]-1-methylethanamine Hydrochloride

Following the procedure of Example 11, 2-bromoethyl-2-chlorophenyl ether was reacted with isopropyl amine (excess) and the reaction mixture processed to give an oil, the free base of the title compound. A portion of the oil was reacted with ethereal hydrogen chloride and the hydrochloride salt recrystallized from methanol-diethyl ether, m.p. 118°–119.5° C. (75%).

Analysis: Calculated for $C_{11}H_{17}NOCl_2$: C, 52.81; H, 6.85; H, 5.60, Found: C, 52.77; H, 6.80; N, 5.64.

Preparation 26

2-(2-Bromoethoxy)naphthalene

Following the procedure of Preparation 10 and substituting β-naphthol for α-naphthol, the title compound was obtained as brown solid which, when triturated with diethyl ether, gave a light brown solid, m.p. 91.5°–93.0° C. in 28% yield.

Analysis: Calculated for $C_{12}H_{11}OBr$: C, 57.40; H, 4.42; Found: C, 57.69; H, 4.40.

Preparation 27

1-Methyl-N-[2-(2-naphthalenyloxy)ethyl]ethanamine, Hydrochloride

Following the procedure of Preparation 11, 2-(2-bromoethoxy)naphthalene was reacted with isopropyl amine (excess) and the reaction mixture processed to give an oil, the free base of the title compound. A portion of the oil was converted to the hydrochloride salt (48%), m.p. 179°–180.5° C.

Analysis: Calculated for $C_{15}H_{20}NOCl$: C, 67.79; H, 7.59; N, 5.27, Found: C, 67.92; H, 7.62; N, 5.34.

Preparation 28

N-[2-[(2,3-Dihydro-1H-inden-5-yl)oxy]ethyl]-1-methylethanamine, Hydrochloride The potassium salt of 5-indanol was prepared from 97.0 g (0.723 mole) of 5-indanol and 40.5 g (0.723 mole) potassium hydroxide in 1 liter of 95% ethanol with stirring for 1 hr at room temperature. To this solution was added 679.2 g (3.615 mole) of 1,2-dibromoethane. The resulting solution heated at reflux overnight. The reaction mixture was filtered and stripped to dryness. The residue was dissolved in chloroform and washed with 10% aqueous sodium hydroxide solution. The chloroform layer was dried and evaporated to dryness to obtain a dark brown oil. A portion of the oil, 46.04 g, was added to 200 ml of isopropylamine and the mixture stirred overnight at room temperature. The excess amine was stripped off to dryness and the residue partitioned between water and chloroform. Removal of chloroform from the chloroform layer produced a dark brown oil, the free base of the title compound. A portion of this oil was converted to the hydrochloride salt with ethereal hydrogen chloride which, on recrystallization from methanol-diethyl ether (24%), melted at 154°–155.5° C.

Analysis: Calculated for $C_{14}H_{22}NOCl$: C, 65.74; H, 8.67; N, 5.48, Found: C, 65.22; H, 8.65; N, 5.43.

Preparation 29

N-[2-[(2,3-Dihydro-1H-inden-4-yl)oxy]ethyl]-1-methylethanamine, Hydrochloride A solution of 24.0 g (0.1 mole) of 4-indanyl-2-bromoethyl ether in 100 ml of isopropylamine was stirred overnight at room temperature. The solution was stripped of excess isopropylamine and the residue partitioned between methylene chloride and water. The methylene chloride layer was evaporated to give a dark brown oil. The oil was reacted with ethereal hydrogen chloride and the mixture filtered. The solid was recrystallized from methanol-diethyl ether to give 16.95 g (66.3%) of white crystals, m.p. 160°–162° C.

Analysis: Calculated for $C_{14}H_{22}NOCl$: C, 65.74; H, 8.67; N, 5.48, Found: C, 65.75; H, 8.68; N, 5.46.

Preparation 30

2-[2-[(2,3-Dihydro-1H-inden-4-yl)oxy]ethyl]-1-H-isoindole-1,3-(2H)-dione

A solution of 54.01 g (0.226 mole) of 4-(2-bromoethoxy) indan and 41.81 g (0.226 mole) of potassium phthalimide in 1200 ml of dimethylformamide was stirred overnight at 85° C. The reaction was filtered and dimethylformamide removed in vacuo in a rotary evaporator to give a white solid. The solid was dissolved in methylene chloride and extracted with water. Methylene chloride was evaporated to give a light brown solid. The solid was triturated with diethyl ether to give 59.3 g light brown solid. A portion of the solid was recrystallized from methylene chloride-ethanol-diethyl ether to give a white crystalline solid, m.p. 128.5°–132.0° C.

Analysis: Calculated for $C_{19}H_{17}NO_3$: C, 74.26; H, 5.58; N, 4.56, Found: C, 73.97; H, 5.46; N, 4.82.

Preparation 31

2-[(2,3-Dihydro-1H-inden-4-yl)oxy]-ethanamine Maleate [1:1]

A solution of 55.28 g (0.18 mole) of 2-[2-[(2,3-dihydro-1H-inden-4-yl)oxy[ethyl]-1H-isoindole-1,3-(2H)dione and 13.0 g (0.22 mole) hydrazine hydrate in 500 ml of 95% ethyl alcohol was heated at reflux for 5 hr. On filtration, a white solid was obtained. The solid was partitioned between chloroform and 10% sodium hydroxide. The ethyl alcohol was removed from the filtrate in a rotary evaporator and the residue was partitioned between chloroform and 10% sodium hydroxide. The chloroform extracts were combined, filtered and evaporated to give an oil (27.20 g) (free base). A portion of the oil was reacted with maleic acid and the salt recrystallized from methanol-diethyl ether to give 3.94 g (57.3%) of white crystalline product; m.p. 150.5°–152° C.

Analysis: Calculated for $C_{15}H_{19}NO_5$: C, 61.42; H, 6.53; N, 4.78, Found: C, 61.35; H, 6.53; N, 4.75.

Preparation 32

N-[2-(3,5-Dichlorophenoxy)ethyl]cyclohexaneamine Hydrochloride

A solution of 27.2 g (0.1 mole) of 2-bromoethyl-3,5-dichlorophenyl ether in 300 ml of cyclohexylamine (excess) was stirred overnight at room temperature. The reaction mixture was filtered and the filtrate stripped to dryness on a rotary evaporator. The residue was partitioned between chloroform and water and between chloroform and 10% sodium hydroxide. The chloroform layer was evaporated to dryness leaving an oil (free base). The oil was dissolved in methanol and reacted with ethereal hydrogen chloride to give 25.8 g (94.2%) solid, m.p. 216.5°–220° C.

Analysis: Calculated for $C_{14}H_{20}NOCl_3$: C, 51.79; H, 6.21; N, 4.31, Found: C, 51.92; H, 6.22; N, 4.34.

Preparation 33

N-Methyl-2-phenoxyethanamine Hydrochloride

A solution of 71.42 g (0.307 mole) of 2-bromoethyl phenylether in excess methylamine was agitated at room temperature overnight in a steel bomb. Unreacted methylamine was allowed to evaporate by opening the bomb. The residue was dissolved in chloroform and washed with water by extraction. Evaporation of chloroform left a light yellow oil (free base) which was dissolved in methanol and reacted with ethereal hydrogen chloride. Recrystallization of the solid from methanol-diethyl ether gave 25.19 g (43.9%) of white crystals, m.p. 173.5°–175.0° C.

Analysis: Calculated for $C_9H_{14}NOCl$: C, 57.60; H, 7.52; N, 7.46, Found: C, 57.38; H, 7.53; N, 7.42.

Preparation 34

N-[-2-(3,5-Dichlorophenoxy)ethyl]butanamine Hydrochloride

A solution of 33.76 g (0.126 mole) of 2-(3,5-dichlorophenoxy)-1-bromoethane in 200 ml of n-butylamine was stirred at 25° C. for 20 hr. The excess n-butylamine was evaporated in vacuo, and the residue was suspended in a mixture of dilute sodium hydroxide and shaken with methylene chloride. The methylene chloride layer was extracted in sequence with two additional portions of dilute sodium hydroxide, one of dilute sulfuric acid and once more with dilute sodium hydroxide. The volume of the methylene chloride layer was reduced to about 150 ml and excess ethereal hydrogen chloride was added. Addition of anhydrous ether gave a white precipitate which was collected and dried under high vacuum (78° C.) to give 19.35 g (51.5%) white crystals, m.p. 195°–196° C.

Analysis: Calculated for $C_{12}H_{18}NOCl_3$: C, 48.26; H, 6.08; N, 4.69, Found: C, 48.17; H, 6.07; N, 4.73.

Preparation 35

N-[-2-(3,5-Dichlorophenoxy)ethyl]propanamine Hydrochloride

The title compound was prepared by the method of Preparation 34 from 2-(3,5-dichlorophenoxy)-1-bromoethane, n-propylamine and hydrogen chloride. The free base was obtained as an oil. The hydrochloride salt melted at 185°–186° C.

Analysis: Calculated for $C_{11}H_{16}NOCl_3$: C, 46.42; H, 5.67; H, 4.92, Found: C, 46.45; H, 5.70; N, 4.92.

Preparation 36

N-[-2-(3,5-Dichlorophenoxy)ethyl]-1,1-dimethylethanamine Maleate

The title compound was prepared by the method of Preparation 34 from 2-(3,5-dichlorophenoxy)-1-bromoethane, and t-butylamine with stirring for 13 days. The free base was obtained as a solid (69%). The maleate salt melted at 202°–203° C.

Analysis: Calculated for $C_{16}H_{21}NO_5$: C, 50.81; H, 5.60; N, 3.70, Found: C, 50.75; H, 5.64; N, 3.68.

Preparation 37

N-[2-(3,5-Dichlorophenoxy)ethyl]-2-methylpropanamine Hydrochloride

The title compound was prepared by the method of Preparation 34 from 2-(3,5-dichlorophenoxy)-1-bromoethane and isobutylamine (72 hr) and hydrogen chloride. The free base was obtained as an oil. The hydrochloride salt melted at 190°–191.5° C.

Analysis: Calculated for $C_{12}H_{18}NOCl_3$: C, 48.26; H, 6.08; N, 4.69, Found: C, 48.38; H, 6.12; N, 4.74.

Preparation 38

N-(1-Methylethyl)-2-[4-(methylthio)phenoxy]ethanamine 4-(Methylthio)phenol is reacted with a large excess of 1,2-dibromethane in the presence of an alkali metal base such as sodium or potassium hydroxide. The product of that reaction, 2-bromoethyl-4-methylthiophenyl ether, is then reacted with isopropylamine as in Preparation 1 to give the title compound.

Preparation 39

N-(1-Methylethyl)-2-[4-(methylsulfinyl)phenoxy]ethanamine

N-(1-Methylethyl)-2-[4-(methylthio)phenoxy]ethanamine (from Preparation 38) is converted to the title compound by reacting with sodium perborate hydrate in 2M sulfuric acid at room temperature. The product is isolated by basifying with sodium hydroxide, extracting with chloroform and evaporating the chloroform layer.

Preparation 40

N-(1-Methylethyl)-2-[4-(methylsulfonyl)phenoxy]ethanamine

N-(1-Methylethyl)-2-[4-(methylthio)phenoxy]ethanamine (from Preparation 38) is converted to the title compound by reacting with sodium perborate hydrate in 2M sulfuric acid at reflux. The product is isolated by basifying with sodium hydroxide, extracting with chloroform and evaporating the chloroform layer.

Preparation 41

N-(1-Methylethyl)-2-[4-(methylsulfonyl)phenoxy]ethanamine Hydrochloride

To a solution of 20.5 g (0.095 mole) of 2-[4-(methylsulfonyl)phenoxy]ethanol (m.p. 96°–98° C.) [prepared by reacting 2-chloroethanol with 4-(methylthio)phenol and potassium carbonate] isolating the 2-[4-(methylthio)phenoxy ethanol, m.p. 55°–56.5° C. and oxidizing with metachloroperoxybenzoic acid] and 12.25 g (0.12 mole) of triethylamine in a mixture of 200 ml of benzene and 500 ml of methylene chloride was slowly added a solution of 14.31 g (0.125 mole) of mesyl chloride in methylene chloride and the solution was stirred at room temperature for about 2 hr. The solvent was removed in vacuo, and the residue was partitioned between methylene chloride and dilute sodium hydroxide. The methylene chloride layer was dried over magnesium sulfate and the solvent was removed in vacuo to give a residue. The residue was dissolved in a mixture of 100 ml of acetonitrile and 300 ml of isopropylamine and the solution stirred at room temperature for about 60 hr. The solvent was removed in vacuo and the residue was partitioned between methylene chloride and dilute sodium hydroxide. The methylene chloride phase was extracted with dilute sulfuric acid. The acidic extract was made basic with 50% sodium hydroxide and the resulting solution was extracted with methylene chloride. The methylene chloride solution was dried over magnesium sulfate and the solvent removed in vacuo to give 17.45 g (62.7%) of the free base of the title compound as a solid. Part of the free base was converted to the hydrochloride salt and the salt was recrystallized from methanol-diethyl ether to give white crystals, m.p. 182°–184° C.

Analysis: Calculated for $C_{12}H_{20}NO_3SCl$: C, 49.06; H, 6.80; N, 4.77, Found: C, 49.00; H, 6.92; N, 4.76.

Preparation 42

N-(1-Methylethyl)-2-(4-nitrophenoxy)ethanamine Hydrochloride p-Nitrophenol was reacted with 1,2-dibromoethane in the presence of sodium hydroxide to obtain 15.9 g impure 2-bromoethyl-4-nitrophenyl ether. The ether was dissolved in 150 ml of isopropylamine and the mixture was stirred at room temperature for 21 hr. The solvent was removed in vacuo and the residue was partitioned between methylene chloride and dilute sodium hydroxide. The methylene chloride was then extracted with several portions of dilute sulfuric acid. The acidic extract was made basic with 50% sodium hydroxide and the basic solution was extracted with methylene chloride. The methylene chloride extract was dried over magnesium sulfate and the solvent was removed in vacuo to give an oil, the free base of the title compound. The free base was dissolved in methanol and the solution was treated with an excess of ethereal hydrogen chloride. White crystalline product, 9.68 g, m.p. 204°–205° C. was obtained.

Analysis: Calculated for $C_{11}H_{17}N_2O_3Cl$: C, 50.68; H, 6.57; N, 10.75, Found: C, 50.70; H, 6.63; N, 10.74.

Preparation 43

2-(4-Acetylphenoxy)-N-(1-methylethyl)ethanamine

4-Hydroxyphenylmethyl ketone is reacted with 1,2-dibromoethane in the presence of base. The product of that reaction, 2-bromoethyl-4-acetylphenyl ether is then reacted with isopropylamine as in Preparation 1 to give the title compound.

Preparation 44

1-Methyl-N-[2-(2,6-dimethylphenoxy)ethyl]ethanamine maleate [1:1]

A solution of 28.43 g (0.171 mole) of 2-(2,6-dimethylphenoxy)ethanol, 23.2 g (0.202 mole) of mesylchloride and an excess of triethylamine in 1 liter of benzene was stirred at room temperature for 2 hr. The solution was filtered and the benzene was removed in vacuo to give an oil. The oil was dissolved in 200 ml of isopropylamine and the solution was stirred at room temperature overnight. The solvent was removed in vacuo to give an oil. The oil was dissolved in methylene chloride and the solution was extracted with dilute sodium hydroxide and then with dilute sulfuric acid. The acidic extract was made basic with 50% sodium hydroxide and the resulting basic solution was extracted with methylene chloride. The methylene chloride solution was dried over magnesium sulfate and the solvent was removed in vacuo to give 26.7 g (75.5%) of the free base of the title compound as an oil. Part of the free base was converted to the maleate salt and the salt was recrystallized from methanol-diethyl ether to give white crystals, m.p. 142°–144° C.

Analysis: Calculated for $C_{17}H_{25}NO_5$: C, 63.14; H, 7.79; N, 4.33, Found: C, 63.13; H, 7.82; N, 4.28.

Preparation 45

N-[2-(4-Fluorophenoxy)ethyl]-2-propanamine Hydrochloride

A mixture of 44.8 g (0.4 mole) of p-fluorophenol, 55.3 g of potassium carbonate, 372.0 g (2.0 mole) of dibromoethane and 1000 ml of acetonitrile was heated overnight at reflux. The reaction mixture was filtered and stripped to dryness on a rotary evaporator. The residue was partitioned between chloroform and 5% sodium hydroxide, repeating the sodium hydroxide wash several times. The chloroform layer was evaporated to give an oil. The oil was added to 150 ml of isopropylamine and the mixture was stirred overnight at room temperature. The unreacted isopropylamine was removed on a rotary evaporator and the residue was partitioned between chloroform and water. Removal of chloroform gave a yellow oil, the free base of the title compound. The free base was dissolved in methanol and converted to the hydrochloride salt with ethereal hydrogen chloride. Recrystallation of the salt from methanol-diethyl ether gave 25.80 g (27.6%) white crystals, m.p. 146°–148° C.

Analysis: Calculated for $C_{11}H_{17}NOFCl$: C, 56.53; H, 7.33; N, 5.99, Found: C, 56.30; H, 7.36; N, 5.87.

Preparation 46

2-[2-[(1-Methylethyl)amino]ethoxy]benzonitrile Maleate

A mixture of 24.75 g (0.21 mole) of 2-cyanophenol, 30.36 g (0.22 mole) of potassium carbonate and 169 g (0.90 mole) of 1,2-dibromoethane in 500 ml of absolute ethanol was refluxed for 18 hr. The solvent was removed in vacuo, and the residue was partitioned between methylene chloride and dilute sodium hydroxide. The methylene chloride phase was dried over magnesium sulfate and the solvent was removed in vacuo. The residue was dissolved in diethylether and the solution cooled. The precipitate was discarded and the other solution was evaporated to give a residue. The residue was dissolved in 300 ml of isopropylamine and the solution was stirred overnight at room temperature. The solvent was removed in vacuo and the residue was partitioned between methylene chloride and dilute sodium hydroxide. The methylene chloride layer was dried over magnesium sulfate and the solvent was evaporated in vacuo to give the free base of the product. The free base was converted to the maleate salt and the salt was recrystallized from methanol-diethyl ether to give 41.76 g (62.1%) of white crystals, m.p. 123°–124.5° C.

Analysis: Calculated for $C_{16}H_{20}N_2O_5$: C, 59.99; H, 6.29; N, 8.75, Found: C, 60.01; H, 6.31; N, 8.74.

Preparation 47

3-[2-[(1-Methylethyl)amino]ethoxy]benzonitrile

Following the procedure of Preparation 46, 3-cyanophenol, potassium carbonate and excess 1,2-dibromoethane are reacted and the product thereof is reacted with isopropylamine to give the title compound.

Preparation 48

4-[2-[(1-Methylethyl)amino]ethoxy]benzonitrile

Following the procedure of Preparation 46, 4-cyanophenol, potassium carbonate and excess 1,2-dibromoethane was reacted and the product thereof is reacted with isopropylamine to give the title compound.

Preparation 49

2-[2-[(1-Methylethyl)amino]ethoxy]benzenecarboxamide

The title compound is obtained by hydrolyzing 2-[2-[(1-methylethyl)amino]ethoxy]benzonitrile (Preparation 46) with hot 70% aqueous sulfuric acid.

Preparation 50

3-[2-[(1-Methylethyl)amino]ethoxy]benzenecarboxamide

The title compound is obtained by hydrolyzing 3-[2-[(1-methylethyl)amino]ethoxy]benzonitrile (Preparation 47) with hot 70% aqueous sulfuric acid.

Preparation 51

4-[2-[(1-Methylethyl)amino]ethoxy]benzenecarboxamide

The title compound is obtained by hydrolyzing 4-[2-[(1-methylethyl)amino]ethoxy]benzonitrile (Preparation 48) with hot 70% aqueous sulfuric acid.

Preparation 52

The following heterocyclic compounds are reacted with 2-chloroacetonitrile:
  piperidine,
  4-methylpiperazine,
  4-phenylmethylpiperazine,
  4-phenyl-1,2,3,6-tetrahydro-1-pyridine,
  4-phenylpiperidine,
  2,6-dimethylpiperidine, and
  4-hydroxy-4-phenylpiperidine
to give the corresponding 1-cyanoethyl derivatives which are then reduced with lithium aluminum hydride or hydrogen over palladium-on-carbon catalyst to give the following 1-(2-aminoethyl) derivatives:
  (a) N-(2-aminoethyl)piperidine,
  (b) 1-(2-aminoethyl)-4-methylpiperazine,
  (c) 1-(2-aminoethyl)-4-phenylpiperazine,
  (d) 1-(2-aminoethyl)-4-phenylmethylpiperazine,
  (e) 1-(2-aminoethyl)-4-phenyl-1,2,3,6-tetrahydropyridine,
  (f) 1-(2-aminoethyl)-4-phenylpiperidine,
  (g) 1-(2-aminoethyl)-2,6-dimethylpiperidine, and
  (h) 1-(2-aminoethyl)-4-hydroxy-4-phenylpiperidine.

Preparation 53

1-(2-Aminoethyl)-4-cyano-4-phenylpiperidine

The title compound is prepared by reacting 4-cyano-4-phenylpiperidine with 1-(2-bromoethyl)phthalimide to obtain 1-[2-(4-cyano-4-phenylpiperidin-1-yl)ethyl]phthalimide and reacting it with hydrazine.

Preparation 54

N-(1-Methylethyl)-2-(3-pyridinyloxy)ethanamine

The title compound is prepared by reacting 3-hydroxypyridine with 2-chloroethanol and the 3-(2-hydroxyethyl) pyridine obtained is reacted with mesyl chloride which is then reacted with isopropylamine.

Preparation 55 a-c

2-Bromoethyl phenylether is reacted with each of the following commercially available amines:
  benzylamine,
  phenethylamine, and
  phenpropylamine
to give the following:
  (a) N-(phenylmethyl)-2-phenoxyethanamine,
  (b) N-(phenylethyl)-2-phenoxyethanamine, and
  (c) N-(phenylpropyl)-2-phenoxyethanamine.

Preparation 56

Each of the following amines are reacted with 2-diethylaminoethyl chloride:
  benzylamine,
  phenethylamine,
  phenpropylamine, and
  phenylbutylamine
to give the following (a) N,N-diethyl-N'-(phenylmethyl)-1,2-ethanediamine,
(b) N,N-diethyl-N'-(phenylethyl)-1,2-ethanediamine,
(c) N,N-diethyl-N'-(phenylpropyl)-1,2-ethanediamine, and
(d) N,N-diethyl-N'-(phenylbutyl)-1,2-ethanediamine.

The following examples 1–45 and 47–91 serve to illustrate the preparation of the compounds useful in treating arrhythmias in the method of this invention. The scope of the invention is, however, not limited thereto. Structures are illustrated in Table 1 and analytical data are in Table 2. Example 46 is representative of novel intermediates in the preparation of active compounds.

EXAMPLE 1

N-[2-(3,4-Dichlorophenoxy)ethyl]-N'-[2-(dimethylamino)ethyl]-N-(1-methylethyl)urea To a solution of 12.25 g (0.05 mole) of 2-(3,4-dichlorophenoxy)-N-(1-methylethyl)ethanamine (oil obtained in Preparation 1) and 1.07 g (0.05 mole) of 1,8-bis(dimethylamino)naphthylene (Proton Sponge ®) in 200 ml of methylene chloride was added dropwise over a 30 minute period, a solution prepared by adding 9.3 g (0.095 mole) of phosgene in 50 ml of benzene to 100 ml of methylene chloride. The reaction solution was stirred for 3 hr at room temperature, after which it was extracted with 1N sulfuric acid. The solvent layer was dried over sodium sulfate-sodium bicarbonate. Solvent was evaporated to give an oil. The oil was dissolved in 250 ml of tetrahydrofuran, and 8.8 g (0.1 mole) of N,N-dimethyl-1,2-ethanediamine in 150 ml of tetrahydrofuran was added dropwise over a 15 min period. The reaction mixture was stirred overnight at room temperature, then stripped to dryness and the residue partitioned between water and methylene chloride. Evaporation of solvent gave a light brown oil which slowly crystallized. Recrystallization from isopropyl ether gave 9.02 g (50%) of white crystalline product, m.p. 53°–56° C. Various salts, such as maleate, oxalate, citrate, fumarate, tartrate and hydrochloride, are prepared therefrom by reaction with maleic, oxalic, citric, fumaric, tartaric and hydrogen chloride, respectively, using an appropriate solvent.

EXAMPLE 2

N-[2-(3,4-Dichlorophenoxy)ethyl]-N'-[2-(dimethylamino)ethyl]-N-(1-methylethyl)urea, Monohydrochloride, Monohydrate This salt was prepared essentially as in Example 1, except the last oil was reacted with ethereal hydrogen chloride followed by recrystallization from methanol-diethyl ether, m.p. 108°–111° C.

EXAMPLE 3

N-[2-(3,5-Dichlorophenoxy)ethyl]-N'-[2-(dimethylamino)ethyl]-N-(1-methylethyl)urea, Maleate [1:1]

To a solution of phosgene in benzene (23.0 ml of 1.9M (0.0436 mole phosgene) and 4.28 g (0.02 mole) of Proton Sponge ® in 100 ml of methylene chloride was added dropwise with stirring a solution of 4.92 g (0.02 mole) of 2-(3,5-dichlorophenoxy-N-(1-methylethyl)ethanamine (oil in Preparation 2) in 100 ml of methylene chloride. After the solution had stirred ¾ hr at room temperature, it was extracted with several portions of 1N sulfuric acid. The methylene chloride layer was dried over sodium sulfate and sodium bicarbonate and then filtered. The solvent was removed under reduced pressure to give an oil. The oil was dissolved in 300 ml of tetrahydrofuran. To the tetrahydrofuran solution was added dropwise 3.52 g (0.04 mole) of N,N-dimethyl-1,2-ethanediamine in 50 ml of tetrahydrofuran with stirring over a 5 minute period. The reaction mixture was stirred over the week-end at room temperature and filtered. Tetrahydrofuran was removed and the residue dissolved in chloroform. The chloroform solution was extracted with water, dried, filtered and evaporated to give an oil, the free base of the title compound. The oil was dissolved in methanol and reacted with maleic acid. Recrystallizaton from methanol-diethyl ether gave 4.70 g (49.1%) of white crystalline product, m.p. 103°–105° C.

EXAMPLE 3A

N-[2-(3,5-Dichlorophenoxy)ethyl]-N'-[2-(dimethylamino)ethyl]-N-(1-methylethyl)urea, Maleate [1:1]

The title compound is prepared, utilizing the latter part of the procedure in Example 3, reacting:

N-[2-(3,5-dichlorophenoxy)ethyl]-N-(1-methylethyl)-carbamic chloride (obtained in Example 46),
N,N-dimethyl-1,2-ethanediamine, and maleic acid; m.p. 103°–105° C.

EXAMPLE 4

N-[2-(3,4-Dichlorophenoxy)ethyl]-N'-[3-(dimethylamino)propyl]-N-(1-methylethyl)urea Oxalate [1:1]

The title compound was prepared by Method A by reacting in sequence:

phosgene, Proton Sponge ®,
2-(3,4-dichlorophenoxy)-N-(1-methylethyl)ethanamine (oil in Preparation 1) and N,N-dimethyl-1,3-propanediamine to give an oil, the free base of the title compound which was then reacted with oxalic acid (39%); m.p. 106°–110° C.

EXAMPLE 5

N-[3-(3,5-Dichlorophenoxy)propyl]-N'-[2-(dimethylamino)ethyl]-N-(1-methylethyl)urea, Oxalate [1:1]

The title compound was prepared by Method A by reacting in sequence:

phosgene, Proton Sponge ®,
3-(3,5-dichlorophenoxy)-N-(1-methylethyl)propanamine (oil in Preparation 3) and N,N-dimethyl-1,2-ethanediamine to give an oil, the free base of the title compound which was then reacted with oxalic acid (49%); m.p. 139°–141° C.

EXAMPLE 6

N'-[2-(Dimethylamino)ethyl]-N-(1-methylethyl)-N-(2-phenoxyethyl)urea, Fumarate [1:1]

The title compound was prepared by Method A by reacting in sequence:

phosgene, proton Sponge ®,
N-(1-methylethyl)-2-phenoxyethanamine (oil in Preparation 4) and N,N-dimethyl-1,2-ethanediamine to give an oil, the free base of the title compound which was then reacted with fumaric acid (27%); m.p. 90°–93.5° C.

EXAMPLE 7

N-[3-(3,5-Dichlorophenoxy)propyl]-N'-[3-(dimethylamino)propyl]-N-(1-methylethyl)urea Citrate [1:1]

The title compound was prepared by Method A, reacting in sequence:
phosgene, Proton Sponge ®,
3-(3,5-dichlorophenoxy)-N-(1-methylethyl)propanamine (oil in Preparation 3) and N,N-dimethyl-1,3-propanediamine to give an oil, the free base of the title compound which was then reacted with citric acid (69%); m.p. 109°–112° C.

EXAMPLE 8

N-[2-(3,5-Dichlorophenoxy)ethyl]-N'-[dimethylamino)propyl]-N-(1-methylethyl)urea Citrate [1:1]

The title compound was prepared by Method A by reacting in sequence:
phosgene, Proton Sponge ®,
2-(3,5-dichlorophenoxy)-N-(1-methylethyl)ethanamine (oil in Preparation 2) and N,N-dimethyl-1,3-propandiamine to give an oil, the free base of the title compound which was then reacted with citric acid (85%); m.p. 126°–128° C.

EXAMPLE 9

N-[2-(3,5-Dichlorophenoxy)ethyl]-N-(1-methylethyl)-N'-[2-[bis-(1-methylethyl)amino]ethyl]urea Hydrochloride [1:1]

The title compound was prepared by Method A by reacting in sequence:
phosgene, Proton Sponge ®.
2-(3,5-dichlorophenoxy)-N-(1-methylethyl)ethanamine (oil in Preparation 2) and N,N-bis-(1-methylethyl)-1,2-ethanediamine (from Preparation 6) and triethylamine to give an oil, the free base of the title compound which was then reacted with ethereal hydrogen chloride (41%); m.p. 187°–189° C.

EXAMPLE 10

N'-[2-(Dimethylamino)ethyl]-N-[(3,4-dimethoxyphenoxy)ethyl]-N-(methylethyl)urea, Fumarate [1:1.5]

The title compound was prepared by Method A by reacting in sequence:
phosgene, Proton Sponge ®,
N-[2-(3,4-dimethoxyphenoxy)ethyl]-1-methylethanamine (oil in Preparation 7) and N,N-dimethyl-1,2-ethanediamine to give an oil, the free base of the title compound which was then reacted with fumaric acid (39.6%); m.p. 128°–130° C.

EXAMPLE 11

N-[2-(2,4-Dichlorophenoxy)ethyl]-N'-[2-(dimethylamino)ethyl]-N-(1-methylethyl)urea, Maleate [1:1]

The title compound was prepared by Method A by reacting in sequence:
phosgene, Proton Sponge ®,
N-[2-(2,4-dichlorophenoxy)ethyl]-1-methylethanamine (solid in Preparation 8 prior to conversion to maleate salt) and N,N-dimethyl-1,2-ethanediamine to give an oil, the free base of the title compound which was then reacted with maleic acid (40.5%); m.p. 131°–132.5° C.

EXAMPLE 12

N-[2-(3,5-Dichlorophenoxy)ethyl]-N'-[(dimethylamino)ethyl]-N-phenylurea, Monohydrochloride The title compound was prepared by Method A by reacting in sequence:
phosgene, Proton Sponge ®,
N-[2-(3,5-dichlorophenoxy)ethyl]benzenamine (obtained by neutralizing the hydrochloride salt of Preparation 9) N,N-dimethyl-1,2-ethanediamine to give an oil, the free base of the title compound which was then reacted with ethereal hydrogen chloride (40%); m.p. 159°–162.5° C.

EXAMPLE 13

N'-[2-(Dimethylamino)ethyl]-N-(1-methylethyl)-N-[2-(1-naphthyleneoxy)ethyl]urea Maleate [1:1]

The title compound was prepared by Method A by reacting in sequence:
phosgene, Proton Sponge ®,
1-methyl-N-[2-(1-napthyleneoxy)ethyl]ethanamine (oil in Preparation 11) and N,N-dimethyl-1,2-ethanediamine to give an oil, the free base of the title compound which was then reacted with maleic acid (75.9%); m.p. 131°–133° C.

EXAMPLE 14

N-[2-(3-Chlorophenoxy)ethyl]-N'-[dimethylamino)ethyl]-N-(1-methylethyl)urea Maleate [1:1]

The title compound was prepared by Method A by reacting in sequence:
phosgene, Proton Sponge ®,
N-[2-(3-chlorophenoxy)ethyl]-1-methylethanamine (oil in Preparation 12) and N,N-dimethyl-1,2-ethanediamine to give an oil, the free base of the title compound which was then reacted with maleic acid (56.3%); m.p. 70.5°–73.0° C.

EXAMPLE 15

N-[2-(2,6-Dichlorophenoxy)ethyl]-N'-[2-(dimethylamino)ethyl]-N-(1-methylethyl)urea The title compound was prepared by Method A by reacting in sequence:
phosgene, Proton Sponge ®,
N-[2-(2,6-dichlorophenoxy)ethyl]-1-methylethanamine (oil in Preparation 13) and N,N-dimethyl-1,2-ethanediamine to give an oil (60.6%).

EXAMPLE 16

N-[2-(3,5-Dichlorophenoxy)ethyl]-N'-[2-(dimethylamino)ethyl]-N'-methyl-N-(1-methylethyl)urea Citrate [1:1]

The title compound was prepared by Method A by reacting in sequence:
phosgene, Proton Sponge ®,
2-(3,5-dichlorophenoxy)-N-(1-methylethyl)ethanamine (oil in Preparation 2) and N,N,N'-trimethyl-1,2-ethanediamine to give an oil, the free base of the title compound which was then reacted with citric acid (71.9%); m.p. 122°–125° C.

EXAMPLE 17

N-[2-(3,5-Dichlorophenoxy)ethyl]-N'-[2-(dimethylamino)ethyl]urea, Fumarate [1:1]

The title compound was prepared by Method A by reacting in sequence:
  phosgene, Proton Sponge ®,
  2-(3,5-dichlorophenoxy)ethanamine (oil in Preparation 15) and N,N-dimethyl-1,2-ethanediamine to give an oil, the free base of the title compound which was then reacted with fumaric acid (46.4%); m.p. 87°–91° C.

EXAMPLE 18

N'-[2-(Dimethylamino)ethyl]-N-[2-(3,5-dimethylphenoxy)ethyl]-N-(1-methylethyl)urea Fumarate [1:1]

Method B Demonstration

To a stirred solution of 8.04 g (0.0496 mole) 1,1'-carbonyldiimidazole in 200 ml of tetrahydrofuran was added dropwise, a solution of 4.3 g (0.049 mole) of N,N-dimethyl-1,2-ethanediamine in 50 ml of tetrahydrofuran. The solution was stirred for 1 hr at room temperature. A solution of 9.76 g (0.047 mole) of N-isopropyl-N-[2-(3,5-dimethylphenoxy)ethyl]amine (oil in Preparation 16) in 100 ml of tetrahydrofuran was added and the solution stirred at room temperature overnight. The reaction mixture was refluxed for 5 hr, quenched in water and extracted with methylene chloride. The organic layer was dried over magnesium sulfate. Removal of solvent under reduced pressure gave the free base as an oil. The free base was dissolved in methanol and fumaric acid added. The fumarate salt was separated and recrystallized from methanol-diethyl ether to give 15.44 g (71.4%) white crystalline solid; m.p. 119°–120° C.

EXAMPLE 19

N-[2-(3,5-Dimethoxyphenoxy)ethyl]-N'-[2-(dimethylamino)ethyl]-N-(1-methylethyl)urea, Fumarate [1:1]

The title compound was prepared by Method B by reacting in sequence:
  N,N-dimethyl-1,2-ethanediamine,
  1,1'-carbonyldiimidazole and
  N-(1-methylethyl)-2-(3,5-dimethoxyphenoxy)ethanamine (oil in Preparation 17) to give an oil, the free base of the title compound which was then reacted with fumaric acid (49%); m.p. 120°–122° C.

EXAMPLE 20

N'-[2-(Dimethylamino)ethyl]-N-[2-(3,4-dimethylphenoxy)ethyl]-N-(1-methylethyl)urea, Fumarate [1:1]

The title compound was prepared by Method B by reacting in sequence:
  N,N-dimethyl-1,2-ethanediamine,
  1,1'-carbonyldiimidazole and
  N-[2-(3,4-dimethylphenoxy)ethyl]-1-methylethanamine (oil in Preparation 18) to give an oil, the free base of the title compound which was then reacted with fumaric acid (75.1%); m.p. 94°–96° C.

EXAMPLE 21

N-[2-(4-Chlorophenoxy)ethyl]-N'-[2-(dimethylamino)ethyl]-N-(1-methylethyl)urea Maleate [1:1]

The title compound was prepared by Method B by reacting in sequence:
  N,N-dimethyl-1,2-ethanediamine,
  1,1'-carbonyldiimidazole and
  N-[2-(4-chlorophenoxy)ethyl]-1-methylethanamine (oil in Preparation 19) to give an oil, the free base of the title compound which was then reacted with maleic aid (60.2%); m.p. 97°–100° C.

EXAMPLE 22

N-[2-(2,5-Dichlorophenoxy)ethyl]-N'-[2-(dimethylamino]ethyl]-N-(1-methylethyl)urea, Maleate [1:1]

The title compound was prepared by Method B, reacting in sequence:
  N,N-dimethyl-1,2-ethanediamine,
  1,1'-carbonyldiimidazole, and
  N-[2-(2,5-dichlorophenoxy)ethyl]-1-methylethanamine (oil in Preparation 20), to give an oil, the free base of the title compound which was then reacted with maleic acid (73.1%); m.p. 133.5°–135° C.

EXAMPLE 23

N-[2-(3,5-Dichlorophenoxy)ethyl]-N-(1-methylethyl)-N'-[2-(4-morpholinyl)ethyl]urea Fumarate [1:1]

The title compound was prepared by Method B, reacting in sequence:
  N-(2-aminoethyl)morpholine,
  1,1'-carbonyldiimidazole, and
  2-(3,5-dichlorophenoxy)-N-(1-methylethyl)ethanamine (oil in Preparation 2), to give an oil, the free base of the title compound which was then reacted with fumaric acid (49%); m.p. 105°–107° C.

EXAMPLE 24

N'-[2-(Dimethylamino)ethyl]-N-(1-methylethyl)-N-[2-(3-trifluoromethylphenoxy)ethyl]urea Fumarate [2:1]

The title compound was prepared by Method B, reacting in sequence:
  N,N-dimethyl-1,2-ethanediamine,
  1,1'-carbonyldiimidazole, and
  1-methyl-N-[2-(3-trifluoromethylphenoxy)ethyl]ethanamine (oil in Preparation 21), to give a solid, the free base of the title compound which was then reacted with fumaric acid; (49.8%) ; m.p. 114°–115° C.

EXAMPLE 25

N-[2-(3,5-Dichlorophenoxy)ethyl]-N'-[2-(dimethylamino)ethyl]-N-methyl urea Maleate [1:1]

The title compound was prepared by Method B, reacting in sequence:
  N,N-dimethyl-1,2-ethanediamine,
  1,1'-carbonyldiimidazole, and
  2-(3,5-dichlorophenoxy)-N-methylethanamine (oil in Preparation 22) to give an oil, the free base of the title compound was then reacted with maleic acid (48.7%); m.p. 105°–107° C.

EXAMPLE 26

N'-[2-(Dimethylamino)ethyl]-N-[2-(3-fluorophenoxy)ethyl]-N-(1-methylethyl)urea Fumarate [1:1]

The title compound was prepared by Method B, reacting in sequence:
N,N-dimethyl-1,2-ethanediamine,
1,1'-carbonyldiimidazole, and
N-[2-(3-fluorophenoxy)ethyl]-1-methylethanamine (oil in Preparation 23), to give an oil, the free base of the title compound which was then reacted with fumaric acid (66.4%); m.p. 106°–108° C.

EXAMPLE 27

N-[2-(2,3-Dichlorophenoxy)ethyl]-N'-[2-(dimethylamino)ethyl]-N-(1-methylethyl)urea Maleate [1:1]

The title compound was prepared by Method B, reacting in sequence:
N,N-dimethyl-1,2-ethanediamine,
1,1'-carbonyldiimidazole, and
N-[2-(2,3-dichlorophenoxy)ethyl]-1-methylethanamine (oil in Preparation 24), to give an oil, the free base of the title compound which was then reacted with maleic acid (69.7%); m.p. 128.5°–130° C.

EXAMPLE 28

N-[2-(2-Chlorophenoxy)ethyl]-N'-[2-(dimethylamino)ethyl]-N-(1-methylethyl)urea Maleate [1:1]

The title compound was prepared by Method B, reacting in sequence:
N,N-dimethyl-1,2-ethanediamine,
1,1'-carbonyldiimidazole, and
N-[2-(2-chlorophenoxy)ethyl]-1-methylethanamine (oil in Preparation 25), to give an oil, the free base of the title compound which was then reacted with maleic acid (73%); m.p. 107.5°–109° C.

EXAMPLE 29

N'-[2-(Dimethylamino)ethyl]-N-(1-methylethyl)-N-[2-(2-naphthalenyloxy)ethyl]urea Hydrochloride The title compound was prepared by Method B, reacting in sequence:
N,N-dimethyl-1,2-ethanediamine,
1,1'-carbonyldiimidazole, and
1-methyl-N-[2-(2-naphthalenyloxy)ethyl]ethanamine (oil of Preparation 27) to give an oil, the free base of the title compound, which was then reacted with ethereal hydrogen chloride (29%); m.p. 169°–171° C.

EXAMPLE 30

N'-[2-(Dimethylamino)ethyl]-N-[2-[(2,3-dihydro-1H-inden-5-yl)oxy]ethyl]-N-(1-methylethyl)urea, Maleate [1:1]

The title compound was prepared by Method B, reacting in sequence:
N,N-dimethyl-1,2-ethanediamine,
1,1'-carbonyldiimidazole, and
N-[2-[(2,3-Dihydro-1H-inden-5-yl)oxy]ethyl]methylethanamine (second oil in Preparation 28), to give an oil, the free base of the title compound which was then reacted with maleic acid (40.9%); m.p. 125.5°–127.0° C.

EXAMPLE 31

N'-[2-(dimethylamino)ethyl]-N-[2-[(2,3-dihydro-1H-inden-4-yl)oxy]ethyl]-N-(1-methylethyl)urea Maleate [1:1]

The title compound was prepared by Method B, reacting in sequence:
N,N-dimethyl-1,2-ethanediamine,
1,1'-carbonyldiimidazole, and
N-[2-[(2,3-dihydro-1H-inden-4-yl)oxy]ethyl]-1-methylethanamine (oil obtained in Preparation 29), to give an oil, the free base of the title compound, which was then reacted with maleic acid (76.8%); m.p. 136.5°–138.0° C.

EXAMPLE 32

N-[2-(3,5-Dichlorophenoxy)ethyl]-N'-methyl-N'-[2-(methylamino)ethyl]-N-(1-methylethyl)urea Maleate [1:1]

The title compound was prepared by Method A, reacting in sequence: phosgene, Proton Sponge®, 2-(3,5-dichlorophenoxy)-N-(1-methylethyl)ethanamine (oil in Preparation 2) and symmetrical dimethylethylenediamine to give an oil, the free base of the title compound which was then reacted with maleic acid (50.1%); m.p. 119.5°–122° C.

EXAMPLE 33

N'-[2-[(2,3-Dihydro-1H-inden-4-yl)oxy]ethyl]-N-[2-(methylamino)ethyl]-N-(1-methyl)urea Fumarate [1:1]

Method C Demonstration

A solution of 3.24 g (0.02 mole) of 1,1'-carbonyldiimidazole and 3.54 g (0.02 mole) of 2-[(2,3-dihydro-1H-inden-4-yl)oxy]ethanamine (free base as oil obtained in Preparation 31) in 100 ml tetrahydrofuran was stirred at room temperature for 5 hr. Symdimethylethylenediamine, 3.06 g (0.03 mole) was added and the solution was heated for 24 hr at reflux. The tetrahydrofuran was removed in a rotary evaporator and the resultant oil partitioned between chloroform and water. The chloroform layer was evaporated to give an oil, the free base of the title compound which was then reacted with fumaric acid. Recrystallization from methanol-diethyl ether gave 4.60 g (56.1%) of white crystalline product after drying at 80° C. overnight in vacuo; m.p. 62.5°–65° C.

EXAMPLE 34

N-n-Butyl-N-[2-(3,5-dichlorophenoxy)ethyl]-N'-[2-(dimethylamino)ethyl]urea Maleate [1:1]

The title compound was prepared by Method B, reacting in sequence:
N,N-dimethylaminoethyl amine,
1,1'-carbonyldiimidazole, and
N-[2-(3,5-dichlorophenoxy)ethyl]butamine (neutralized product of Preparation 34), to give an oil, the free base of the title compound which was then reacted with maleic acid (71.1%); m.p. 128°–129° C.

EXAMPLE 35

N-[2-(3,5-Dichlorophenoxy)ethyl]-N'-[2-(dimethylamino)ethyl]-N-propylurea Maleate [1:1]

The title compound was prepared by Method B, reacting in sequence:

N,N-dimethylaminoethyl amine,
1,1'-carbonyldiimidazole, and
N-[2-(3,5-dichlorophenoxy)ethyl]propanamine (from Preparation 35), to give an oil, the free base of the title compound which was then reacted with maleic acid; m.p. 119°–121° C.

EXAMPLE 36

N-Cyclohexyl-N-[2-(3,5-dichlorophenoxy)ethyl]-N'-[2-(dimethylamine)ethyl]urea Maleate [1:1]

The title compound was prepared by Method A from:
phosgene, Proton Sponge ®,
N-[2-(3,5-dichlorophenoxy)ethyl]cyclohexanamine, and
N-N-dimethyl-1,2-ethanediamine, to give an oil, the free base of the title compound which was then reacted with fumaric acid (60.1%); m.p. 125.5°–126.5° C.

EXAMPLE 37

N-[2-(3,5-Dichlorophenoxy)ethyl]-N'-[2-(dimethylamino)ethyl]-N-(2-methylpropyl)urea Maleate [1:1]

The title compound was prepared by Method B by reacting in sequence:
N,N-dimethylaminoethylamine,
1,1'-carbonyldiimidazole, and
N-[2-(3,5-dichlorophenoxy)ethyl]-2-methyl-1-propanamine (oil in Preparation 37) to give an oil, the free base of the title compound which was then reacted with maleic acid (69.9%); m.p. 117.5°–119° C.

EXAMPLE 38

N-[2-(3,5-Dichlorophenoxy)ethyl]-N'-[2-(dimethylamino)ethyl]-N-(1,1-dimethylethyl)urea Maleate The title compound is prepared by Method B by reacting in sequence:
N,N-dimethylaminoethylamine,
1,1'-carbonyldiimidazole, and
N-[2-(3,5-dichlorophenoxy)ethyl]-1,1-dimethylethanamine (free base from Preparation 36) to give the free base of the title compound which was then reacted with maleic acid.

EXAMPLE 39

N'-[2-(3,5-Dichlorophenoxy)ethyl]-N-[2-(dimethylamino)ethyl]-N-methylurea Maleate [1:1]

The title compound was prepared by Method C, reacting in sequence:
2-(3,5-dichlorophenoxy)ethanamine (oil in Preparation 15)
1,1'-carbonyldiimidazole, and
N,N,N'-trimethylethylenediamine, to give an oil, the free base of the title compound which was then reacted with maleic acid (94.4%); m.p. 86°–89° C.

EXAMPLE 40

N-[2-(3,5-dichlorophenoxy)ethyl]-N-(1-methylethyl)-N'-(2-aminoethyl)urea Maleate [1:1]

The title compound was prepared by Method A, reacting in sequence:
phosgene, Proton Sponge ®,
2-(3,5-dichlorophenoxy)-N-(1-methylethyl)ethanamine (oil in Preparation 2), and
ethylenediamine to give an oil, the free base of the title compound, which was then reacted with maleic acid (44.3%); m.p., 153°–154° C.

EXAMPLE 41

N'-[2-(Diethylamino)ethyl]-N-methyl-N-(2-phenoxyethyl)urea Oxalate [2:3]

The title compound was prepared by Method A, reacting in sequence:
phosgene, Proton Sponge ®,
N-methyl-2-phenoxyethanamine (oil in Preparation 33),
and N,N-diethylethylenediamine, to give an oil, the free base of the title compound which was then reacted with oxalic acid (11.7%); m.p. 107°–108° C.

EXAMPLE 42

N'-[2-(Diethylamino)ethyl]-N-methyl-N-(2-phenoxyethyl)urea Hydrate [2:1]

A solution of N'-[2-diethylamino)ethyl]-N-methyl-N-(2-phenoxyethyl)urea oxalate [2:3] from Example 41 was dissolved in water and the solution made basic with an excess of 2M sodium hydroxide solution. The solution was extracted with methylene chloride and the methylene chloride solution dried over magnesium sulfate. The methylene chloride was removed in vacuo to give an oil. The oil was stored under high vacuum at 25° C. for 6 days. Nuclear magnetic resonance showed the product had ½ equivalent of water present.

EXAMPLE 43

N-Methyl-N-(2-phenoxyethyl)-N'-[2-(1-pyrrolidinyl)ethyl]urea Oxalate [1:1]

The title compound was prepared by Method A, reacting in sequence:
phosgene,
N-(1-methyl)-2-phenoxyethanamine (oil in Preparation 33)
and N-(2-aminoethyl)pyrrolidine, to give an oil, the free base of the title compound which was then reacted with oxalic acid; m.p., 117.5°–118.5° C.

The title compound was also prepared by Method B, reacting in sequence:
N-(2-aminoethyl)pyrrolidine,
1,1'carbonyldiimidazole, and
N-(1-methyl)-2-phenoxyethanamine (oil in Preparation 33), to give an oil, the free base of the title compound which was then reacted with oxalic acid; m.p. 117.5°–118.5° C.

EXAMPLE 44

N-[2-(3,5-Dichlorophenoxy)ethyl]-N'-[2-(diethylamino)ethyl]-N-(1-methylethyl)urea Tartrate [1:1]

The title compound was prepared by Method B, reacting in sequence:
diethylaminoethylamine,
1,1'-carbonyldiimidazole, and
2-(3,5-dichlorophenoxy)-N-(1-methylethyl)ethanamine to give an oil, the free base of the title compound which was then reacted with tartaric acid (55%); m.p. 119°–120° C.

EXAMPLE 45

N-[2-(3,5-Dichlorophenoxy)ethyl]-N'-[2-(dimethylamino)ethyl]-N-(1-methylethyl)urea Hydrate [2:1]

A solution of N-[2-(3,5-dichlorophenoxy)ethyl]-N'-[2-(dimethylamino)ethyl]-N-(1-methylethyl)urea Maleate [1:1], from Example 3A, was basified with 2M sodium hydroxide solution and extracted with methylene chloride. The methylene chloride layer was dried over magnesium sulfate and evaporated under vacuum to give an oil. Nuclear magnetic resonance measurements showed the product had ½ equivalent of water present.

EXAMPLE 46

N-[2-(3,5-Dichlorophenoxy)ethyl]-N-(1-methylethyl)-carbamic chloride

A solution of 4.53 g (0.018 mole) of 2-(3,5-dichlorophenoxy)-N-(1-methylethyl)ethanamine (oil obtained in Preparation 1), 3.92 g (0.040 moles) phosgene in 21 ml solution of benzene and 3.92 g (0.018 mole) of 1,8-bis(dimethylamino)naphthalene (proton sponge) in 200 ml of methylene chloride was stirred overnight at room temperature. The reaction mixture was extracted with 1N sulfuric acid and the methylene chloride layer thereafter dried over sodium sulfate-sodium carbonate. Evaporation of solvent gave an oil which, when triturated with hexane, gave 1.91 g (34.2%) g of solid. The solid forms a gum on exposure to air which prevents measurement of melting point by conventional means.

Analysis: Calculated for $C_{12}H_{14}NO_2Cl_3$: C, 46.40; H, 4.54; N, 4.51, Found: C, 46.51; H, 4.50; N, 4.50.

EXAMPLE 47

N-[2-(3,5-Dichlorophenoxy)ethyl]-N'-[2-(dimethylamino)ethyl]-N-(1-methylethyl)thiourea, Hemifumarate, Hemihydrate The title compound was prepared by Method A as follows: To a solution of 6.42 g (0.03 mole) of Proton Sponge ® [1,8-bis(dimethylamino)naphthalene and 4.90 g (0.043 mole) of thiophosgene in 300 ml of methylene chloride was added dropwise a solution of 7.30 g (0.03 mole) of 2-(3,5-dichlorophenoxy)-N-(1-methylethyl)ethanamine (oil in Preparation 2) in methylene chloride. The solution was stirred 2 hours additionally at room temperature and then extracted several times with 1N aqueous sulfuric acid solution. The methylene chloride layer was dried over anhydrous potassium carbonate, filtered and rotary-evaporated to give a dark brown oil. The oil was dissolved in tetrahydrofuran, 5.28 g (0.06 mole) of unsym. N,N-dimethylethylenediamine added and the solution stirred overnight at room temperature. The reaction mixture was stripped to dryness and partitioned several times between chloroform and 10% aqueous sodium hydroxide. Removal of chloroform gave an oil, the free base of the title compound. The fumarate salt was prepared and recrystallized several times from methanol-diethyl ether. After drying overnight at 80° C., 3.14 g (23.5%) of a white crystalline solid was obtained, m.p. 153° C.

EXAMPLE 48

N'-[2-(Diethylamino)ethyl]-N-(1-methylethyl)-N-(2-phenoxyethyl)thiourea Oxalate [1:1]

The title compound was prepared by Method A and the procedure of Example 47 by reacting in sequence: thiophosgene, Proton Sponge ®,
N-(1-methylethyl)-2-phenoxyethanamine (free base oil in Preparation 4), and
N,N-diethylethylenediamine to give an oil, the free base of the title compound which was then reacted with oxalic acid to give the oxalate, (16.4%), m.p. 117°-117.5° C.

EXAMPLE 49

N'-[2-(Dimethylamino)ethyl]-N-(1-methylethyl)-N-[2-(1-naphthalenyloxy)ethyl]thiourea Maleate [1:1]

The title compound was prepared by Method A and the procedure of Example 47 by reacting in sequence: thiophosgene, Proton Sponge ®,
1-methyl-N-[2-(1-naphthenyloxy)ethyl]ethanamine (oil in Preparation 11), and
N,N-dimethylethylenediamine to give an oil, the free base of the title compound which was then converted to the maleate salt (27.0%), m.p. 130°-131° C.

EXAMPLE 50

N'-[2-(Diethylamino)ethyl]-N-methyl-N-(2-phenoxyethyl)thiourea, Citrate Hemihydrate The title compound was prepared by Method A and the procedure of Example 47 by reacting in sequence: thiophosgene, Proton Sponge ®,
N-methyl-2-phenoxyethanamine (oil in Preparation 33) and
N,N-diethylethylenediamine to give an oil, the free base of the title compound which was then converted to the citrate hemihydrate salt, (25%) a pink salt, m.p. 106°-110° C.

EXAMPLE 51

N'-[2-(3,5-Dichlorophenoxy)ethyl]-N-[2-(dimethylamino)ethyl]-N-(1-methylethyl)urea Maleate The title compound was prepared by Method A, reacting in sequence:
phosgene, Proton Sponge ®,
2-(3,5-dichlorophenoxy)ethanamine (oil in Preparation 15),
N'-isopropyl-N,N-dimethylethylenediamine and triethylamine to give an oil, the free base of the title compound which was then reacted with maleic acid (24.4%), m.p. 115°-116° C.

EXAMPLE 52

N'-[2-[(2,3-Dihydro-1H-inden-4-yl)oxy]ethyl]-N-[2-(dimethylamino)ethyl]-N-(1-methylethyl)urea Maleate [1:1]

(Method D Demonstration)

To a solution of 39.2 g (0.05 mole) of phosgene (40 ml of 12% phosgene in benzene) in methylene chloride was added 6.5 g (0.05 mole) of N'-isopropyl-N,N-dimethylethylenediamine also in methylene chloride over a 30 minute period. The solution was stirred for one hour at room temperature. To the reaction mixture were added dropwise with stirring 8.85 g (0.05 mole) of N-[2-[(2,3-dihydro-1H-inden-4-yl)oxy]ethyl]ethanamine (oil in Preparation 31) and 10.1 g (0.1 mole) of triethylamine over a 30 min period. The reaction mixture was stirred overnight at room temperature and thereafter extracted with aqueous 10% sodium hydroxide solution. The methylene chloride layer was then extracted with 1N sulfuric acid. The acid layer was made alkaline and extracted with chloroform. The chloroform layer was evaporated to give an oil, the free base of the title compound. The free base was converted to the maleate salt which was recrystallized from methanol-diethyl ether to give 2.41 g (10.7%) of white crystalline product, m.p. 118°–120° C.

EXAMPLE 53

N-[2-(3,4-Dichlorophenoxy)ethyl]-N'-[2-(dimethylamino)ethyl]-N-(1-methylethyl)thiourea When in the procedure of Example 3, equal molar amounts of thiophosgene are substituted for phosgene, the title compound is obtained.

EXAMPLE 54 a-h

When in the procedure of Example 3, equal molar substitutions of thiophosgene for phosgene and the following for 2-(3,4-dichlorophenoxy)-N-(1-methylethyl)ethanamine are made:
3-(3,5-dichlorophenoxy)-N-(1-methylethyl)propanamine (oil in Preparation 3),
N-[2-(3,4-dimethoxyphenoxy)ethyl]-1-methylethanamine (oil in Preparation 7),
N-[2-(2,4-dichlorophenoxy)ethyl]-1-methylethanamine (solid in Preparation 8 prior to conversion to maleate salt),
N-[2-(3,5-dichlorophenoxy)ethyl]benzeneamine (neutralized Preparation 9),
N-[2-(3-chlorophenoxy)ethyl]-1-methylethanamine (oil in Preparation 12),
N-[2-(2,6-dichlorophenoxy)ethyl]-1-methylethanamine (oil in Preparation 13),
2-(3,5-dichlorophenoxy)ethanamine (oil in Preparation 15), and
N-[2-(3,5-dichlorophenoxy)ethyl]cyclohexanamine (oil in Preparation 32),
there are obtained:
(a) N-[3-(3,5-dichlorophenoxy)propyl]-N'-[2-dimethylamino)ethyl]-N-(1-methylethyl)thiourea and the oxalate salt prepared therefrom,
(b) N'-[2-(dimethylamino)ethyl]-N-[(3,4-dimethoxyphenoxy)ethyl]-N-(methylethyl)thiourea and the fumarate salt thereof,
(c) N-[2-(2,4-dichlorophenoxy)ethyl]-N'-[2-(dimethylamino)ethyl]-N-(1-methylethyl)thiourea and the maleate salt thereof,
(d) N-[2-(3,5-dichlorophenoxy)ethyl]-N'-[2-(dimethylamino)ethyl]-N-phenylthiourea and the hydrochloride salt thereof,
(e) N-[2-(3-chlorophenoxy)ethyl]-N'-[2-(dimethylamino)ethyl]-N-(1-methylethyl)thiourea and the maleate salt thereof,
(f) N-[2-(2,6-dichlorophenoxy)ethyl]-N'-]2-(dimethylamino)ethyl]-N-(1-methylethyl)thiourea,
(g) N-[2-(3,5-dichlorophenoxy)ethyl]-N'-[2-(dimethylamino)ethyl]thiourea and the fumarate salt thereof, and
(h) N-cyclohexyl-N-[2-(3,5-dichlorophenoxy)ethyl]-N'-[2-(dimethylamino)ethyl]thiourea and the maleate salt thereof.

EXAMPLE 55 a-c

When in the procedure of Example 3, equal molar substitutions of thiophosgene for phosgene, N,N-dimethyl-1,3-propanamine for N,N-dimethyl-1,2-ethanediamine and the following for 2-(3,5-dichlorophenoxy)-N-(1-methylethyl)ethanamine are made:
2-(3,4-dichlorophenoxy)-N-(1-methylethyl)ethanamine (oil in Preparation 1),
3-(3,5-dichlorophenoxy)-N-(1-methylethyl)propanamine (oil in Preparation 3), and
2-(3,5-dichlorophenoxy)-N-(1-methylethyl)ethanamine (oil in Preparation 2),
there are obtained:
(a) N-[2-(3,4-dichlorophenoxy)ethyl]-N'-[3-(dimethylamino)propyl]-N-(1-methylethyl)thiourea and the maleate salt thereof,
(b) N-[3-(3,5-dichlorophenoxy)propyl]-N'-[3-(dimethylamino)propyl]-N-(1-methylethyl)thiourea and the maleate salt, and
(c) N-[2-(3,5-dichlorophenoxy)ethyl]-N'-[3-(dimethylamino)propyl]-N-(1-methylethyl)thiourea and the maleate salt thereof.

EXAMPLE 56

N-[2-(3,5-Dichlorophenoxy)ethyl]-N'-[2-(dimethylamino)ethyl]-N'-methyl-N-(1-methylethyl)thiourea Citrate The title compound is prepared by Method A by reacting in sequence:
thiophosgene, Proton Sponge ®,
2-(3,5-dichlorophenoxy)-N-(1-methylethyl)ethanamine (oil in Preparation 2), and
N,N,N'-trimethyl-1,2-ethanediamine to give the free base which is then reacted with citric acid to give the title compound.

EXAMPLE 57

N-[2-(3,5-Dichlorophenoxy)ethyl]-N'-methyl-N'-[2-(methylamino)ethyl]-N-(1-methylethyl]thiourea Maleate The title compound is prepared by Method A by reacting in sequence:
thiophosgene, Proton Sponge ®,
2-(3,5-dichlorophenoxy)-N-(1-methylethyl)ethanamine (oil in Preparation 2) and symmetrical-dimethylethyleneamine to give the free base which is then reacted with maleic acid to give the title compound.

EXAMPLE 58

N-[2-(3,5-Dichlorophenoxy)ethyl]-N-(1-methylethyl)-N'-(2-aminoethyl)thiourea

The title compound is prepared by Method A, reacting in sequence:
thiophosgene, Proton Sponge ®,
2-(3,5-dichlorophenoxy)-N-(1-methylethyl)ethanamine (oil in Preparation 2) and ethylenediamine.

EXAMPLE 59

N-Methyl-N-(2-phenoxyethyl)-N'-[2-(1-pyrrolidinyl)ethyl]thiourea

The title compound was prepared by Method A, reacting in sequence:
thiophosgene, Proton Sponge ®,
N-(1-methyl)-2-phenoxyethanamine (oil in Preparation 33) and, N-(2-aminoethyl)pyrrolidine.

EXAMPLE 60

N'-[2-(Dimethylamino)ethyl]-N-(1-methylethyl)-N-[2-[4-(methylthio)phenoxy]ethyl]urea Maleate The title compound is prepared by Method B. reacting in sequence:

N,N-dimethyl-1,2-ethanediamine,
1,1'-carbonyldiimidazole, and
N-(1-methylethyl)-2-(4-methylthiophenoxy)ethanamine from Preparation 38 to give the free base of the title compound which is then reacted with maleic acid.

EXAMPLE 61

N'-[2-(Diethylamino)ethyl]-N-(1-methylethyl)-N-[2-[4-(methylsulfinyl)phenoxy]ethyl]urea Maleate The title compound is prepared by Method B, reacting in sequence:
N,N-diethyl-1,2-ethanediamine,
1,1'-carbonyldiimidazole, and
N-(1-methylethyl)-2-(4-methylsulfinylphenoxy)ethanamine from Preparation 39 to give the title compound which is then reacted with maleic acid.

EXAMPLE 62

N'-[2-(Diethylamino)ethyl]-N-(1-methylethyl)-N-[2-[4-(methylsulfonyl)phenoxy]ethyl]urea Maleate The title compound is prepared by Method B, reacting in sequence:
N,N-diethyl-1,2-ethanediamine,
1,1-carbonyldiimidazole, and
N-(1-methylethyl)-2-(4-methylsulfonylphenoxy)ethanamine from Preparation 40 to give the title compound which is then reacted with maleic acid.

EXAMPLE 63

N'-[2-(Dimethylamino)ethyl]-N-(1-methylethyl)-N-[2-(4-nitrophenoxy)ethyl]urea Maleate The title compound is prepared by Method B, reacting in sequence:
N,N-dimethyl-1,2-ethanediamine,
1,1'-carbonyldiimidazole, and
N-(1-methylethyl)-2-(4-nitrophenoxy)ethanamine from Preparation 41 to give the free base of the title compound which is then reacted with maleic acid.

EXAMPLE 64

N'-[2-(Dimethylamino)ethyl]-N-(1-methylethyl)-N-[2-(4-aminophenoxy)ethyl]urea

N'-[2-(dimethylamino)ethyl]-N-(1-methylethyl)-N-[2-(4-nitrophenoxy)ethyl]urea, free base in Example 62, is hydrogenated over palladium-on-charcoal catalyst to give the title compound.

EXAMPLE 65

N-[2-(4-Acetylphenoxy)ethyl]-N'-[2-(dimethylamino)ethyl]-N-(1-methylethyl)urea, Maleate The title compound is prepared by Method B, reacting in sequence:
N,N-dimethyl-1,2-ethanediamine,
1,1'-carbonyldiimidazole, and
2-(4-acetylphenoxy)-N-(1-methylethyl)ethanamine from Preparation 42 to give the free base of the title compound which is then reacted with maleic acid.

EXAMPLE 66

N'-[2-(Dimethylamino)ethyl]-N-[2-(2,6-dimethylphenoxy)ethyl]-N-(1-methylethyl)urea Oxalate [1:1]

The title compound was prepared by Method B by reacting in sequence:
N,N-dimethyl-1,2-ethanediamine,
1,1'-carbonyldiimidazole, and
1-methyl-N-[2-(2,6-dimethylphenoxy)ethyl]ethanamine (oil in Preparation 44) to give an oil, the free base of the title compound which was then reacted with maleic acid (82.6%); m.p. 139°–140° C. (with decomposition).

EXAMPLE 67

N'-[2-(Diethylamino)ethyl]-N-(1-methylethyl)-N-[2-[4-(methylsulfonyl)phenoxy]ethyl]urea Fumarate [2:3]

The title compound was prepared by Method B by reacting in sequence:
N,N-diethyl-1,2-ethanediamine,
1,1'-carbonyldiimidazole, and
N-(1-methylethyl)-2-[4-(methylsulfonyl)phenoxy]ethanamine (solid free base from Preparation 41) to give the free base of the title compound which was then reacted with fumaric acid to give the fumarate salt. The salt was recrystallized from methanol-ether to give white solid. The solid was dried under high vacuum at 78° C. with melting. On cooling, a noncrystalline glossy solid formed.

EXAMPLE 68

N'-[2-(Dimethylamino)ethyl]-N-(1-methylethyl)-N-[2-(4-nitrophenoxy)ethyl]urea

The title compound was prepared by Method B by reacting in sequence:
N,N-dimethyl-1,2-ethanediamine,
1,1'-carbonyldiimidazole, and
N-(1-methylethyl)-2-(4-nitrophenoxy)ethanamine hydrochloride (oil in Preparation 42) to give an oil, the free base of the title compound. The free base was recrystallized from a mixture of methylene chloride-ether-hexane to give white crystalline solid (66.3%), m.p. 64°–67° C.

EXAMPLE 69

N'-[2-(Dimethylamino)ethyl]-N-(1-methylethyl)-N-[2-[4-(methylsulfonyl)phenoxy]ethyl]urea Fumarate [1:1]

The title compound was prepared by reacting in sequence:
N,N-dimethyl-1,2-ethanediamine,
1,1'-carbonyldiimidazole, and
N-(1-methylethyl)-2-[4-(methylsulfonyl)phenoxy]ethanamine hydrochloride (free base as solid in Preparation 41) to give an oil, the free base of the title compound which was then reacted with fumaric acid to give white crystalline solid (48.3%), m.p. 78°–88° C.

EXAMPLE 70

N'-[2-(Diethylamino)ethyl]-N-[2-(4-fluorophenoxy)ethyl]-N-(1-methylethyl)urea Oxalate Hemihydrate The title compound was prepared by Method B by reacting in sequence:
N,N-diethyl-1,2-ethanediamine,
1,1'-carbonyldiimidazole, and
N-[2-(4-fluorophenoxy)ethyl]-2-propanamine (yellow oil in Preparation 45) to give an oil, the free base of the title compound. The oil was dissolved in diethyl ether, mixed with 2 g Silica Gel and filtered. The ether was evaporated to give an oil which was reacted with oxalic acid to yield white crystalline solid (46%), m.p. 97°–99° C.

EXAMPLE 71

N'-[2-(Dimethylamino)ethyl]-N-[2-(4-fluorophenoxy)ethyl]-N-(1-methylethyl)urea Oxalate [1:1]

The title compound was prepared by Method B by reacting in sequence:
N,N-dimethyl-1,2-ethanediamine,
1,1'-carbonyldiimidazole, and
N-[2-(4-fluorophenoxy)ethyl]-2-propanamine (oil in Preparation 45) to give an oil, the free base of the title compound which was reacted with oxalic acid to yield white crystals (85.3%), m.p. 144°–145° C.

EXAMPLE 72

N-[2-(2-Cyanophenoxy)ethyl]-N'-[2-(diethylamino)ethyl]-N-(1-methylethyl)urea Oxalate [1:1]

The title compound was prepared by Method B by reacting in sequence:
N,N-diethyl-1,2-ethanediamine,
1,1'-carbonyldiimidazole, and
2-[2-[(1-methylethyl)amino]ethoxy]benzonitrile (free base in Preparation 46) to give an oil, the free base of the title compound which was reacted with oxalic acid to give white crystals (38.7%), m.p. 111°–113° C. with decomp.

EXAMPLE 73

N'-[2-(Dimethylamino)ethyl]-N-(1-methylethyl)-N-[2-(4-acetylaminophenoxy)ethyl]urea The title compound is prepared by reacting the compound of Example 64: N'-[2-dimethylamino)ethyl]-N-(1-methylethyl)-N-[2-(4-aminophenoxy)ethyl]urea with acetyl chloride in triethylamine.

EXAMPLE 74

N-[2-(4-Benzoylaminophenoxy)ethyl]-N'-[2-(dimethylamino)ethyl]-N-(1-methylethyl)urea The title compound is prepared by reacting the compound of Example 64: N'-[2-(dimethylamino)ethyl]-N-(1-methylethyl)-N-[2-(4-aminophenoxy)ethyl]urea with benzoyl chloride in triethylamine.

EXAMPLE 75

N-(1-Methylethyl)-N-(2-phenoxyethyl)-N'-[2-(1-piperidinyl)ethyl]urea

The title compound is prepared by Method A, reacting in sequence:
phosgene,
N-(1-methylethyl)-2-phenoxyethanamine, and
N-(2-aminoethyl)piperidine.

EXAMPLE 76

N-(1-Methylethyl)-N-(2-phenoxyethyl)-N'-[2-(4-methyl-1-piperazinyl)ethyl]urea

The title compound is prepared by Method A, reacting in sequence:
phosgene,
N-(1-methylethyl)-2-phenoxyethanamine, and
1-(2-aminoethyl)-4-methylpiperazine.

EXAMPLE 77

N-(1-Methylethyl)-N-(2-phenoxyethyl)-N'-[2-(4-phenyl-1-piperazinyl)ethyl]urea

The title compound is prepared by Method A, reacting in sequence:
phosgene,
N-(1-methylethyl)-2-phenoxyethanamine, and
1-(2-aminoethyl)-4-phenylpiperazine.

EXAMPLE 78

N-(1-Methylethyl)-N-(2-phenoxyethyl)-N'-[2-(4-phenylmethyl-1-piperazinyl)ethyl]urea The title compound is prepared by Method A, reacting in sequence:
phosgene,
N-(1-methylethyl)-2-phenoxyethanamine, and
1-(2-aminoethyl)-4-phenylmethylpiperazine

EXAMPLE 79

N-(1-Methylethyl)-N-(2-phenoxyethyl)-N'-[2-(4-phenyl-1,2,3,6-tetrahydro-1-pyridinyl)ethyl]urea The title compound is prepared by Method A, reacting in sequence:
phosgene,
N-(1-methylethyl)-2-phenoxyethanamine, and
1-(2-aminoethyl)-4-phenyl-1,2,3,6-tetrahydropyridine.

EXAMPLE 80

N-(1-Methylethyl)-N-(2-phenoxyethyl)-N'-[2-(4-phenyl-1-piperidinyl)ethyl]urea

The title compound is prepared by Method A, reacting in sequence:
phosgene,
N-(1-methylethyl)-2-phenoxyethanamine, and
1-(2-aminoethyl)-4-phenylpiperidine.

EXAMPLE 81

N-(1-Methylethyl)-N-(2-phenoxyethyl)-N'-[2-(2,6-dimethyl-1-piperidinyl)ethyl]urea The title compound is prepared by Method A, reacting in sequence:
phosgene,
N-(1-methylethyl)-2-phenoxyethanamine, and
1-(2-aminoethyl)-2,6-dimethylpiperidine.

EXAMPLE 82

N-(1-Methylethyl)-N-(2-phenoxyethyl)-N'-[2-(4-hydroxy-4-phenyl-1-piperidinyl)ethyl]urea The title compound is prepared by Method A, reacting in sequence:
phosgene,
N-(1-methylethyl)-2-phenoxyethanamine, and
1-(2-aminoethyl)-4-hydroxy-4-phenylpiperidine.

EXAMPLE 83

N'-[2-(4-Cyano-4-phenyl-1-piperidinyl)ethyl]-N-(1-methylethyl)-N-(2-phenoxyethyl)urea The title compound is prepared by Method A, reacting in sequence:
phosgene,
N-(1-methylethyl)-2-phenoxyethanamine, and
1-(2-aminoethyl)-4-cyano-4-phenylpiperidine.

EXAMPLE 84

N-[2-(3-Cyanophenoxy)ethyl]-N'-[2-(diethylamino)ethyl]-N-(1-methylethyl)urea

The title compound is prepared by Method B, reacting in sequence:
N,N-diethyl-1,2-ethanediamine, 1,1'-carbonyldiimidazole, and 3-[2-[(1-methylethyl)amino]ethoxy]benzonitrile.

EXAMPLE 85

N-[2-(4-Cyanophenoxy)ethyl]-N'-[2-(diethylamino)ethyl]-N-(1-methylethyl)urea

The title compound is prepared by Method B, reacting in sequence:

N,N-diethyl-1,2-ethanediamine, 1,1'-carbonyldiimidazole, and

4-[2-[(1-methylethyl)amino]ethoxy]benzonitrile.

EXAMPLE 86

N-[2-[2-(Aminocarbonyl)phenoxy]ethyl]-N'-[2-(diethylamino)ethyl]-N-(1-methylethyl)urea The title compound is prepared by Method B, reacting in sequence:

N,N-diethyl 1,2-ethanediamine, 1,1'-carbonyldiimidazole, and

2-[2-[(1-methylethyl)amino]ethoxy]benzenecarboxamide.

EXAMPLE 87

N-[2-[3-(Aminocarbonyl)phenoxy]ethyl]-N'-[2-(diethylamino)ethyl]-N-(1-methylethyl)urea The title compound is prepared by Method B, reacting in sequence:

N,N-diethyl-1,2-ethanediamine, 1,1'-carbonyldiimidazole, and

3-[2-[(1-methylethyl)amino]ethoxy]benzenecarboxamide.

EXAMPLE 88

N-[2-[4-(Aminocarbonyl)phenoxy]ethyl]-N'-[2-(diethylamino)ethyl]-N-(1-methylethyl)urea The title compound is prepared by Method B, reacting in sequence:

N,N-diethyl-1,2-ethanediamine, 1,1'-carbonyldiimidazole, and

4-[2-[(1-methylethyl)amino]ethoxy]benzenecarboxamide.

EXAMPLE 89

N'-[2-(Dimethylamino)ethyl]-N-(1-methylethyl)-N-[2-(3-pyridinyloxy)ethyl]urea

The title compound is prepared by Method B, reacting in sequence:

N,N-diethyl-1,2-ethanediamine, 1,1'-carbonyldiimidazole, and

N-(1-methylethyl)-2-(3-pyridinyloxy)ethanamine.

EXAMPLE 90 a-c

When in the procedure of Method B, N,N-diethyl-1,2-ethanediamine and 1,1'-carbonyldiimidazole are reacted and each of the following are reacted with the product thereof:

N-(phenylmethyl)-2-phenoxyethanamine,

N-(phenylethyl)-2-phenoxyethanamine, and

N-(phenylpropyl)-2-phenoxyethanamine there are obtained:

(a) N'-[2-(diethylamino)ethyl]-N-(2-phenoxyethyl)-N-(phenylmethyl)urea, (b) N'-[2-(diethylamino)ethyl]-N-(2-phenoxyethyl)-N-(phenylethyl)urea, and (c) N'-[2-(diethylamino)ethyl]-N-(2-phenoxyethyl)-N-phenylpropyl)urea.

EXAMPLE 91 a-d

When in the procedure of Method A, phosgene and N-(1-methylethyl)-2-phenoxyethanamine are reacted and each of the following are reacted with the product thereof:

N,N-diethyl-N'-(phenylmethyl)-1,2-ethanediamine,

N,N-diethyl-N'-(phenylethyl)-1,2-ethanediamine,

N,N-diethyl-N'-(phenylpropyl)-1,2-ethanediamine, and

N,N-diethyl-N'-(phenylbutyl)-1,2-ethanediamine, there are obtained:

(a) N-[2-(diethylamino)ethyl]-N'-(1-methylethyl)-N'-(2-phenoxyethyl)-N-(phenylmethyl)urea, (b) N-[2-(diethylamino)ethyl]-N'-(1-methylethyl)-N'-(2-phenoxyethyl)-N-(phenylethyl)urea, (c) N-[2-(diethylamino)ethyl]-N'-(1-methylethyl)-N'-(2-phenoxyethyl)-N-(phenylpropyl)urea, and (d) N-[2-(diethylamino)ethyl]-N'-(1-methylethyl)-N'-(2-phenoxyethyl)-N-phenylbutyl)urea.

EXAMPLE 92

N'-[2-(Ethylamino)ethyl]-N-(1-methylethyl)-N-(2-phenoxyethyl)urea

The title compound is prepared by Method A, reacting in sequence:

phosgene, Proton Sponge ®,

N-(1-methylethyl)-2-phenoxyethanamine (oil in Preparation 4), and a large excess of monoethylethylenediamine.

TABLE 1

$$Ar-O-alk^1-N-\overset{R^1}{\underset{|}{\phantom{N}}}-\overset{X}{\underset{\|}{C}}-N-\overset{R^2}{\underset{|}{\phantom{N}}}alk^2-N\overset{R^3}{\underset{R^4}{\diagdown}}$$

| Ex. No. | Ar | alk¹ | R¹ | X | R² | alk² | —NR³R⁴ | Salt | M.P. °C. |
|---|---|---|---|---|---|---|---|---|---|
| 1 | 3,4-Cl₂—C₆H₃ | —(CH₂)₂— | —CH(CH₃)₂ | O | H | —(CH₂)₂— | N—CH₃, CH₃ | — | 53–56 |
| 2 | 3,4-Cl₂—C₆H₅ | —(CH₂)₂— | —CH(CH₃)₂ | O | H | —(CH₂)₂— | N—CH₃, CH₃ | HCl.½H₂O | 108–111 |
| 3 | 3,5-Cl₂—C₆H₃ | —(CH₂)₂— | —CH(CH₃)₂ | O | H | —(CH₂)₂— | N—CH₃,CH₃ | maleate | 103–105 |
| 4 | 3,4-Cl₂—C₆H₃ | —(CH₂)₂— | —CH(CH₃)₂ | O | H | —(CH₂)₃— | N—CH₃, CH₃ | oxalate | 106–110 |
| 5 | 3,5-Cl₂—C₆H₃ | —(CH₂)₂— | —CH(CH₃)₂ | O | H | —(CH₂)₃— | N—CH₃, CH₃ | oxalate | 139–141 |
| 6 | —C₆H₅— | —(CH₂)₂— | —CH(CH₃)₂ | O | H | —(CH₂)₂— | N—CH₃, CH₃ | fumarate | 90–93.5 |
| 7 | 3,5-Cl₂—C₆H₃ | —(CH₂)₃— | —CH(CH₃)₂ | O | H | —(CH₂)₂— | N—CH₃, CH₃ | fumarate | 109–112 |
| 8 | 3,5-Cl₂—C₆H₃ | —(CH₂)₃— | —CH(CH₃)₂ | O | H | —(CH₂)₃— | N—CH₃, CH₃ | citrate | 126–128 |
| 9 | 3,5-Cl₂—C₆H₃ | —(CH₂)₂— | —CH(CH₃)₂ | O | H | —(CH₂)₂— | N—CH₃, CH₃ | HCl | 187–189 |
| 10 | 3,4-(OCH₃)₂—C₆H₃ | —(CH₂)₂— | —CH(CH₃)₂ | O | H | —(CH₂)₂— | N—[—CH(CH₃)₂]₂ | 1.5 fumarate | 128–130 |
| 11 | 2,4-Cl₂—C₆H₃ | —(CH₂)₂— | —CH(CH₃)₂ | O | H | —(CH₂)₂— | N—CH₃, CH₃ | maleate | 131–132.5 |
| 12 | 3,5-Cl₂—C₆H₃ | —(CH₂)₂— | —C₆H₅ | O | H | —(CH₂)₂— | N—CH₃, CH₃ | HCl | 159–162.5 |
| 13 | 1-C₁₀H₇ | —(CH₂)₂— | —CH(CH₃)₂ | O | CH₃ | —(CH₂)₂— | N—CH₃, CH₃ | maleate | 131–133 |
| 14 | 3-Cl—C₆H₄— | —(CH₂)₂— | —CH(CH₃)₂ | O | H | —(CH₂)₂— | N—CH₃, CH₃ | maleate | 70.5–73.0 |
| 15 | 2,6-Cl₂—C₆H₃ | —(CH₂)₂— | H | O | H | —(CH₂)₂— | N—CH₃, CH₃ | — | — |
| 16 | 3,5-Cl₂—C₆H₃ | —(CH₂)₂— | —CH(CH₃)₂ | O | H | —(CH₂)₂— | N—CH₃, CH₃ | citrate | 122–125 |
| 17 | 3,5-Cl₂—C₆H₃ | —(CH₂)₂— | —CH(CH₃)₂ | O | H | —(CH₂)₂— | N—HC, CH₃ | fumarate | 87–91 |
| 18 | 3,5-(CH₃)₂—C₆H₃ | —(CH₂)₂— | —CH(CH₃)₂ | O | H | —(CH₂)₂— | N—CH₃, CH₃ | fumarate | 119–120 |
| 19 | 3,5-(OCH₃)₂—C₆H₃ | —(CH₂)₂— | —CH(CH₃)₂ | O | H | —(CH₂)₂— | N—CH₃, CH₃ | fumarate | 120–122 |
| 20 | 3,4-(CH₃)₂—C₆H₃ | —(CH₂)₂— | —CH(CH₃)₂ | O | H | —(CH₂)₂— | N—CH₃, CH₃ | fumarate | 94–96 |
| 21 | 4-Cl—C₆H₄— | —(CH₂)₂— | —CH(CH₃)₂ | O | H | —(CH₂)₂— | N—CH₃, CH₃ | maleate | 97–100 |
| 22 | 2,5-Cl₂—C₆H₃ | —(CH₂)₂— | —CH(CH₃)₂ | O | H | —(CH₂)₂— | N—CH₃, CH₃ | fumarate | 133.5–135 |
| 23 | 3,5-Cl₂—C₆H₃ | —(CH₂)₂— | —CH(CH₃)₂ | O | H | —(CH₂)₂— | 4-morpholine | maleate | 105–107 |
| 24 | 3 CF₃—C₆H₃ | —(CH₂)₂— | —CH(CH₃)₂ | O | H | —(CH₂)₂— | N—CH₃, CH₃ | 0.5 fumarate | 114–115 |
| 25 | 3,5-Cl₂—C₆H₃ | —(CH₂)₂— | —CH₃ | O | CH₃ | —(CH₂)₂— | N—CH₃, CH₃ | maleate | 105–107 |
| 26 | 3 F—C₆H₄— | —(CH₂)₂— | —CH(CH₃)₂ | O | H | —(CH₂)₂— | N—CH₃, CH₃ | maleate | 106–108 |
| 27 | 2,3-Cl₂—C₆H₃ | —(CH₂)₂— | —C₃H₇ | O | H | —(CH₂)₂— | N—CH₃, CH₃ | maleate | 128.5–130 |
| 28 | 2 Cl—C₆H₄— | —(CH₂)₂— | —C₆H₁₁ | O | H | —(CH₂)₂— | N—CH₃, CH₃ | maleate | 107.5–109 |
| 29 | 2-C₁₀H₇ | —(CH₂)₂— | —CH₂CH(CH₃)₂ | O | H | —(CH₂)₂— | N—CH₃, CH₃ | HCl | 169–171 |
| 30 | 5-C₉H₆O[a] | —(CH₂)₂— | —C(CH₃)₃ | O | H | —(CH₂)₂— | N—CH₃, CH₃ | maleate | 125.5–127.0 |
| 31 | 4-C₉H₆O[b] | —(CH₂)₂— | H | O | H | —(CH₂)₂— | N—CH₃, CH₃ | maleate | 136.5–138–0 |
| 32 | 3,5-Cl₂—C₆H₃ | —(CH₂)₂— | —CH(CH₃)₂ | O | CH₃ | —(CH₂)₂— | N—CH₃, CH₃ | maleate | 119.5–122 |
| 33 | 4-C₉H₆O[b] | —(CH₂)₂— | —CH(CH₃)₂ | O | CH₃ | —(CH₂)₂— | N—H, CH₃ | fumarate | 62.5,65 |
| 34 | 3,5-Cl₂—C₆H₃ | —(CH₂)₂— | —C₄H₉ | O | H | —(CH₂)₂— | N—H, CH₃ | maleate | 128–129 |
| 35 | 3,5-Cl₂—C₆H₃ | —(CH₂)₂— | —C₃H₇ | O | H | —(CH₂)₂— | N—CH₃, CH₃ | maleate | 119–121 |
| 36 | 3,5-Cl₂—C₆H₃ | —(CH₂)₂— | —C₆H₁₁ | O | H | —(CH₂)₂— | N—CH₃, CH₃ | maleate | 125.5–126.5 |
| 37 | 3,5-Cl₂—C₆H₃ | —(CH₂)₂— | —CH₂CH(CH₃)₂ | O | H | —(CH₂)₂— | N—CH₃CH₃ | maleate | 117.5–119 |
| 38 | 3,5-Cl₂—C₆H₃ | —(CH₂)₂— | —CH(CH₃)₂ | O | H | —(CH₂)₂— | N—CH₃, CH₃ | maleate | — |
| 39 | 3,5-Cl₂—C₆H₃ | —(CH₂)₂— | H | O | CH₃ | —(CH₂)₂— | N—CH₃, CH₃ | maleate | 86–89 |
| 40 | 3,5-Cl₂—C₆H₃ | —(CH₂)₂— | —CH(CH₃)₂ | O | H | —(CH₂)₂— | N—H, H | maleate | 153–154 |
| 41 | C₆H₅— | —(CH₂)₂— | —CH₃ | O | H | —(CH₂)₂— | N—C₂H₅, C₂H₅ | 1.5 oxalate | 107–108 |
| 42 | C₆H₅— | —(CH₂)₂— | —CH₃ | O | H | —(CH₂)₂— | N—C₂H₅, C₂H₅ | 0.5 H₂O | — |
| 43 | C₆H₅— | —(CH₂)₂— | —CH₃ | O | H | —(CH₂)₂— | 1-pyrrolidinyl | oxalate | 117.5–118.5 |
| 44 | 3,5-Cl₂—C₆H₃ | —(CH₂)₂— | —CH(CH₃)₂ | O | H | —(CH₂)₂— | N—C₂H₅, C₂H₅ | tartrate | 119–120 |
| 45 | 3,5-Cl₂—C₆H₃ | —(CH₂)₂— | —CH(CH₃)₂ | O | H | —(CH₂)₂— | N—CH₃, CH₃ | 1½ H₂O | — |

TABLE 1-continued $$Ar-O-alk^1-\underset{\underset{R^1}{|}}{N}-\underset{\underset{X}{||}}{C}-\underset{\underset{R^2}{|}}{N}-alk^2-N\underset{R^4}{\overset{R^3}{\diagdown}}$$

| Ex. No. | Ar | alk¹ | R¹ | X | R² | alk² | —NR³R⁴ | Salt | M.P. °C. |
|---|---|---|---|---|---|---|---|---|---|
| 47 | 3,5-Cl₂—C₆H₃— | —(CH₂)₂— | —CH(CH₃)₂ | S | H | —(CH₂)₂— | N—CH₃, CH₃ | ½ fumarate ½ H₂O | 153 |
| 48 | C₆H₅— | —(CH₂)₂— | —CH(CH₃)₂ | S | H | —(CH₂)₂— | N—C₂H₅, C₂H₅ | oxalate | 117–117.5 |
| 49 | 1-C₁₀H₇— | —(CH₂)₂— | —CH(CH₃)₂ | S | H | —(CH₂)₂— | N—CH₃, CH₃ | maleate | 130–131 |
| 50 | C₆H₅— | —(CH₂)₂— | —CH₃ | S | H | —(CH₂)₂— | N—C₂H₅, C₂H₅ | citrate. | 106–110 |
| 51 | 3,5-Cl₂—C₆H₃— | —(CH₂)₂— | H | O | —CH(CH₃)₂ | —(CH₂)₂— | N—CH₃, CH₃ | maleate ½ H₂O | 115–116 |
| 52 | 4-C₉H₁₀(b) | —(CH₂)₂— | H | O | —CH(CH₃)₂ | —(CH₂)₂— | N—CH₃, CH₃ | maleate | 118–120 |
| 53 | 3,5-Cl₂—C₆H₃— | —(CH₂)₂— | —CH(CH₃)₂ | S | H | —(CH₂)₂— | N—CH₃, CH₃ | — | — |
| 54(a) | 3,4-Cl₂—C₆H₃— | —(CH₂)₂— | —CH(CH₃)₂ | S | H | —(CH₂)₂— | —N(CH₃)₂ | oxalate | — |
| (b) | 3,5-Cl₂—C₆H₃— | —(CH₂)₃— | —CH(CH₃)₂ | S | H | —(CH₂)₂— | —N(CH₃)₂ | fumarate | — |
| (c) | 3,4-(OCH₃)₂— | —(CH₂)₂— | —CH(CH₃)₂ | S | H | —(CH₂)₂— | —N(CH₃)₂ | maleate | — |
| (d) | 2,4-Cl₂—C₆H₃— | —(CH₂)₂— | —H | S | H | —(CH₂)₂— | —N(CH₃)₂ | HCl | — |
| (e) | 3-Cl—C₆H₄— | —(CH₂)₂— | —(CH₃)₂ | S | H | —(CH₂)₂— | —N(CH₃)₂ | maleate | — |
| (f) | 2,6-Cl₂—C₆H₃— | —(CH₂)₂— | —CH(CH₃)₂ | S | H | —(CH₂)₂— | —N(CH₃)₂ | — | — |
| (g) | 3,5-Cl₂—C₆H₃— | —(CH₂)₂— | —CH(CH₃)₂ | S | H | —(CH₂)₂— | —N(CH₃)₂ | fumarate | — |
| (h) | 3,4-Cl₂—C₆H₃— | —(CH₂)₂— | —C₆H₁₁ | S | H | —(CH₂)₂— | —N(CH₃)₂ | maleate | — |
| 55(a) | 3,5-Cl₂—C₆H₃— | —(CH₂)₃— | —CH(CH₃)₂ | S | H | —(CH₂)₃— | —N(CH₃)₂ | maleate | — |
| (b) | 3,5-Cl₂—C₆H₃— | —(CH₂)₂— | —CH(CH₃)₂ | S | H | —(CH₂)₃— | —N(CH₃)₂ | maleate | — |
| (c) | 3,5-Cl₂—C₆H₃— | —(CH₂)₂— | —CH(CH₃)₂ | S | H | —(CH₂)₂— | —N(CH₃)₂ | maleate | — |
| 56 | 3,5-Cl₂—C₆H₃— | —(CH₂)₂— | —CH(CH₃)₂ | S | —CH₃ | —(CH₂)₂— | —N(CH₃)₂ | citrate | — |
| 57 | 3,5-Cl₂—C₆H₃— | —(CH₂)₂— | —CH(CH₃)₂ | S | —CH₃ | —(CH₂)₂— | —N(CH₃)₂ | maleate | — |
| 58 | 3,5-Cl₂—C₆H₃— | —(CH₂)₂— | —CH(CH₃)₂ | S | H | —(CH₂)₂— | —NHCH₃ | — | — |
| 59 | C₆H₅— | —(CH₂)₂— | —CH₃ | S | H | —(CH₂)₂— | —NH₂ | — | — |
| 60 | 4-CH₃S—C₆H₄— | —(CH₂)₂— | —CH(CH₃)₂ | S | H | —(CH₂)₂— | 1-pyrrolidinyl | maleate | — |
| 61 | 4-[CH₃S(O)]— C₆H₄— | —(CH₂)₂— | —CH(CH₃)₂ | O | H | —(CH₂)₂— | —N(CH₃)₂ | maleate | — |
| 62 | 4-[CH₃S(O)₂]— C₆H₄— | —(CH₂)₂— | —CH(CH₃)₂ | O | H | —(CH₂)₂— | —N(C₂H₅)₂ | maleate | — |
| 63 | 4-NO₂—C₆H₄— | —(CH₂)₂— | —CH(CH₃)₂ | O | H | —(CH₂)₂— | —N(CH₃)₂ | — | — |
| 64 | 4-NH₂—C₆H₄— | —(CH₂)₂— | —CH(CH₃)₂ | O | H | —(CH₂)₂— | —N(CH₃)₂ | — | — |
| 65 | 4-[CH₃C(O)]— C₆H₄— | —(CH₂)₂— | —CH(CH₃)₂ | O | H | —(CH₂)₂— | —N(CH₃)₂ | maleate | — |
| 66 | 2,6-(CH₃)₃—C₆H₃ | —(CH₂)₂— | —CH(CH₃)₂ | O | H | —(CH₂)₂— | —N(CH₃)₃ | oxalate | 139–140 dec. |
| 67 | 4-[CH₃S(O)₂]— C₆H₄ | —(CH₂)₂— | —CH(CH₃)₂ | O | H | —(CH₂)₂— | =N(C₂H₅)₂ | fumarate[2:3] | ca 78 |
| 68 | 4-NO₂—C₆H₄— | —(CH₂)₂— | —CH(CH₃)₂ | O | H | —(CH₂)₂— | —N(CH₃)₂ | — | 64–67 |
| 69 | 4-[CH₃S(O)₂]— C₆H₄— | —(CH₂)₂— | —CH(CH₃)₂ | O | H | —(CH₂)₂— | —N(CH₃)₂ | fumarate | 78–88 |
| 70 | 4-F—C₆H₄— | —(CH₂)₂— | —CH(CH₃)₂ | O | H | —(CH₂)₂— | —N(C₂H₅)₂ | — | 97–99 |
| 71 | 4-F—C₆H₄— | —(CH₂)₂— | —CH(CH₃)₂ | O | H | —(CH₂)₂— | —N(CH₃)₂ | oxalate. ½ H₂O | 144–145 |
| 72 | 2-CN—C₆H₄— | —(CH₂)₂— | —CH(CH₃)₂ | O | H | —(CH₂)₂— | —N(C₂H₅)₂ | oxalate | 111–113 |
| 73 | 4-[CH₃C(O)NH₂]— C₆H₄— | —(CH₂)₂— | —CH(CH₃)₂ | O | H | —(CH₂)₂— | —N(CH₃)₂ | — | — |

TABLE 1-continued $$Ar-O-alk^1-N-C-N-alk^2-N\begin{array}{c}R^3\\ \diagdown\\ R^4\end{array}$$
$$\phantom{Ar-O-alk^1-N}\underset{R^1}{|}\underset{X}{\|}\underset{R^2}{|}$$

| Ex. No. | Ar | alk¹ | R¹ | X | R² | alk² | —NR³R⁴ | Salt | M.P. °C. |
|---|---|---|---|---|---|---|---|---|---|
| 74 | 4-[C₆H₅C(O)NH₂—] | —(CH₂)₂— | —CH(CH₃)₂ | O | H | —(CH₂)₂— | —N(CH₃)₂ | — | — |
| 75 | C₆H₅— | —(CH₂)₂— | —CH(CH₃)₂ | O | H | —(CH₂)₂— | 1-piperidinyl | — | — |
| 76 | C₆H₅— | —(CH₂)₂— | —CH(CH₃)₂ | O | H | —(CH₂)₂— | 4-CH₃—piperazin-1-yl | — | — |
| 77 | C₆H₅— | —(CH₂)₂— | —CH(CH₃)₂ | O | H | —(CH₂)₂— | 4-C₆H₅—piperazin-1-yl | — | — |
| 78 | C₆H₅— | —(CH₂)₂— | —CH(CH₃)₂ | O | H | —(CH₂)₂— | 4-C₆H₅CH₂—piperazin-1-yl | — | — |
| 79 | C₆H₅— | —(CH₂)₂— | —CH(CH₃)₂ | O | H | —(CH₂)₂— | 4-C₆H₅—1,2,3,6-tetrahydro-pyridin-1-yl | — | — |
| 80 | C₆H₅— | —(CH₂)₂— | —CH(CH₃)₂ | O | H | —(CH₂)₂— | 4-C₆H₅—piperazin-1-yl | — | — |
| 81 | C₆H₅— | —(CH₂)₂— | —CH(CH₃)₂ | O | H | —(CH₂)₂— | 2,6-(CH₃)₂—piperidin-1-yl | — | — |
| 82 | C₆H₅— | —(CH₂)₂— | —CH(CH₃)₂ | O | H | —(CH₂)₂— | 4-OH—4-C₆H₅—piperidin-1-yl | — | — |
| 83 | C₆H₅— | —(CH₂)₂— | —CH(CH₃)₂ | O | H | —(CH₂)₂— | 4-CN—4-C₆H₅—piperidin-1-yl | — | — |
| 84 | 3-CN—C₆H₅— | —(CH₂)₂— | —CH(CH₃)₂ | O | H | —(CH₂)₂— | —N(C₂H₅)₂ | — | — |
| 85 | 4-CN—C₆H₅— | —(CH₂)₂— | —CH(CH₃)₂ | O | H | —(CH₂)₂— | —N(C₂H₅)₂ | — | — |
| 86 | 2-[NH₂C(O)]—C₆H₅— | —(CH₂)₂— | —CH(CH₃)₂ | O | H | —(CH₂)₂— | —N(C₂H₅)₂ | — | — |
| 87 | 3-[NH₂C(O)]—C₆H₅— | —(CH₂)₂— | —CH(CH₃)₂ | O | H | —(CH₂)₂— | —N(C₂H₅)₂ | — | — |
| 88 | 4-[NH₂C(O)]—C₆H₅— | —(CH₂)₂— | —CH(CH₃)₂ | O | H | —(CH₂)₂— | —N(C₂H₅)₂ | — | — |
| 89 | 3-pyridinyl | —(CH₂)₂— | —CH(CH₃)₂ | O | H | —(CH₂)₂— | —N(C₂H₅)₂ | — | — |
| 90(a) | C₆H₅— | —(CH₂)₂— | C₆H₅CH₂— | O | H | —(CH₂)₂— | —N(C₂H₅)₂ | — | — |
| (b) | C₆H₅— | —(CH₂)₂— | C₆H₅(CH₂)₂— | O | H | —(CH₂)₂— | —N(C₂H₅)₂ | — | — |
| (c) | C₆H₅— | —(CH₂)₂— | C₆H₅(CH₂)₃— | O | H | —(CH₂)₂— | —N(C₂H₅)₂ | — | — |
| 91(a) | C₆H₅— | —(CH₂)₂— | —CH(CH₃)₂ | O | C₆H₅—CH₂— | —(CH₂)₂— | —N(C₂H₅)₂ | — | — |
| (b) | C₆H₅— | —(CH₂)₂— | —CH(CH₃)₂ | O | C₆H₅(CH₂)₂— | —(CH₂)₂— | —N(C₂H₅)₂ | — | — |
| (c) | C₆H₅— | —(CH₂)₂— | —CH(CH₃)₂ | O | C₆H₅(CH₂)₃— | —(CH₂)₂— | —N(C₂H₅)₂ | — | — |
| (d) | C₆H₅— | —(CH₂)₂— | —CH(CH₃)₂ | O | C₆H₅(CH₂)₄— | —(CH₂)₂— | —N(C₂H₅)₂ | — | — |
| 92 | C₆H₅— | —(CH₂)₂— | —CH(CH₃)₂ | O | H | —(CH₂)₂— | —NHC₂H₅ | — | — |

TABLE 2

| Ex. No. | Empirical Formula | Analytical Data | | | | | |
|---|---|---|---|---|---|---|---|
| | | Calculated | | | Found | | |
| | | C | H | N | C | H | N |
| 1 | $C_{16}H_{25}N_3O_2Cl_2$ | 53.04 | 6.96 | 14.60 | 52.94 | 6.97 | 11.63 |
| 2 | $C_{16}H_{27}N_3O_{2.5}Cl_3$ | 47.12 | 6.67 | 10.31 | 47.02 | 6.55 | 10.41 |
| 3 | $C_{20}H_{29}N_3O_6Cl_2$ | 50.22 | 6.11 | 8.78 | 50.20 | 6.09 | 8.80 |
| 4 | $C_{19}H_{29}N_3O_6Cl_2$ | 48.93 | 6.27 | 9.01 | 48.87 | 6.25 | 9.03 |
| 5 | $C_{19}H_{29}N_3O_6Cl_2$ | 48.93 | 6.27 | 9.01 | 48.59 | 6.26 | 6.89 |
| 6 | $C_{20}H_{31}N_3O_6$ | 58.66 | 7.63 | 10.26 | 58.45 | 7.62 | 10.25 |
| 7 | $C_{24}H_{37}N_3O_9Cl_2$ | 49.49 | 6.40 | 7.21 | 49.19 | 6.40 | 7.14 |
| 8 | $C_{23}H_{35}N_3O_9Cl_2$ | 48.60 | 6.21 | 7.39 | 48.54 | 6.19 | 7.37 |
| 9 | $C_{20}H_{34}N_3O_2Cl_3$ | 52.81 | 7.53 | 9.24 | 52.45 | 7.51 | 9.08 |
| 10 | $C_{24}H_{37}N_3O_{10}$ | 54.64 | 7.07 | 7.97 | 54.89 | 7.23 | 8.12 |
| 11 | $C_{20}H_{29}N_3O_6Cl_2$ | 50.22 | 6.11 | 8.78 | 50.08 | 6.13 | 8.84 |
| 12 | $C_{19}H_{24}N_3O_2Cl_3$ | 52.73 | 5.59 | 9.71 | 52.51 | 5.61 | 9.79 |
| 13 | $C_{24}H_{33}N_3O_6$ | 62.73 | 7.24 | 9.14 | 62.75 | 7.26 | 9.12 |
| 14 | $C_{20}H_{30}N_3O_6Cl$ | 54.11 | 6.81 | 9.46 | 54.03 | 6.84 | 9.36 |
| 15 | $C_{16}H_{25}N_3O_2Cl_2$ | 53.04 | 6.96 | 11.60 | 52.54 | 6.95 | 11.79 |
| 16 | $C_{23}H_{35}N_3O_9Cl_2$ | 48.60 | 6.21 | 7.39 | 48.61 | 6.17 | 7.35 |
| 17 | $C_{17}H_{23}N_3O_6Cl_2$ | 46.80 | 5.31 | 9.63 | 46.56 | 5.26 | 9.67 |
| 18 | $C_{22}H_{33}N_3O_6$ | 60.39 | 8.06 | 9.60 | 60.38 | 8.11 | 9.58 |
| 19 | $C_{22}H_{35}N_3O_8$ | 56.28 | 7.51 | 8.95 | 56.24 | 7.49 | 8.94 |
| 20 | $C_{22}H_{35}N_3O_6$ | 60.39 | 8.06 | 9.60 | 60.45 | 8.18 | 9.79 |
| 21 | $C_{20}H_{30}N_3O_6Cl$ | 54.11 | 6.81 | 9.46 | 53.73 | 6.69 | 9.64 |
| 22 | $C_{20}H_{29}N_3O_6Cl_2$ | 50.22 | 6.11 | 8.78 | 50.13 | 6.16 | 8.98 |
| 23 | $C_{22}H_{31}N_3O_7Cl_2$ | 50.78 | 6.00 | 8.07 | 50.45 | 6.00 | 7.56 |
| 24 | $C_{19}H_{28}N_3O_4F_3$ | 54.41 | 6.73 | 10.02 | 54.41 | 6.68 | 9.82 |
| 25 | $C_{18}H_{25}N_3O_6Cl_2$ | 48.01 | 5.60 | 9.33 | 47.91 | 5.61 | 9.38 |
| 26 | $C_{20}H_{30}N_3O_6F$ | 56.20 | 7.07 | 9.83 | 56.38 | 7.12 | 9.85 |
| 27 | $C_{20}H_{29}N_3O_6Cl_2$ | 50.22 | 6.11 | 8.78 | 50.34 | 6.08 | 8.82 |
| 28 | $C_{20}H_{30}N_3O_6Cl$ | 54.11 | 6.81 | 9.46 | 53.95 | 6.81 | 9.47 |
| 29 | $C_{20}H_{30}N_3O_2Cl$ | 63.22 | 7.95 | 11.06 | 63.19 | 7.96 | 11.07 |
| 30 | $C_{23}H_{35}N_3O_6$ | 61.45 | 7.85 | 9.35 | 61.52 | 7.90 | 9.32 |
| 31 | $C_{23}H_{35}N_3O_6$ | 61.45 | 7.85 | 9.35 | 61.21 | 7.88 | 9.44 |
| 32 | $C_{20}H_{29}N_3O_6Cl_2$ | 50.22 | 6.11 | 8.78 | 50.16 | 6.12 | 8.84 |
| 33 | $C_{20}H_{29}N_3O_6$ | 58.96 | 7.17 | 10.31 | 58.51 | 7.17 | 10.22 |
| 34 | $C_{21}H_{31}N_3O_6Cl_2$ | 51.23 | 6.35 | 8.53 | 51.30 | 6.40 | 8.65 |
| 35 | $C_{20}H_{29}N_3O_6Cl_2$ | 50.22 | 6.11 | 8.78 | 49.91 | 6.03 | 9.09 |
| 36 | $C_{23}H_{33}N_3O_6Cl_2$ | 53.29 | 6.42 | 8.11 | 53.15 | 6.41 | 8.12 |
| 37 | $C_{21}H_{31}N_3O_6Cl_2$ | 51.23 | 6.35 | 8.53 | 51.35 | 6.38 | 8.62 |
| 38 | $C_{21}H_{31}N_3O_6Cl_2$ | — | — | — | — | — | — |
| 39 | $C_{18}H_{25}N_3O_6Cl_2$ | 48.01 | 5.60 | 9.33 | 48.10 | 5.64 | 9.35 |
| 40 | $C_{18}H_{25}N_3O_6Cl_2$ | 48.01 | 5.60 | 9.33 | 47.92 | 5.59 | 9.34 |
| 41 | $C_{19}H_{30}N_3O_8$ | 53.26 | 7.06 | 9.81 | 53.11 | 7.07 | 9.87 |
| 42 | $C_{16}H_{28}N_3O_{2.5}$ | 63.55 | 9.33 | 13.90 | 63.92 | 9.25 | 13.76 |
| 43 | $C_{18}H_{27}N_3O_6$ | 56.68 | 7.14 | 11.02 | 56.41 | 7.11 | 11.00 |
| 44 | $C_{22}H_{35}N_3O_8$ | 48.89 | 6.53 | 7.78 | 48.83 | 6.60 | 7.71 |
| 45 | $C_{16}H_{26}N_3O_{2.5}Cl_2$ | 51.76 | 7.06 | 11.32 | 51.78 | 6.82 | 11.37 |
| 47 | $C_{18}H_{28}N_3O_{3.5}SCl_2$ | 48.54 | 6.34 | 9.43 | 48.96 | 6.13 | 9.57 |
| 48 | $C_{20}H_{33}N_3O_5S$ | 56.18 | 7.78 | 4.83 | 56.14 | 7.80 | 4.85 |
| 49 | $C_{24}H_{33}N_3O_5S$ | 60.61 | 6.69 | 8.84 | 60.64 | 7.01 | 8.83 |
| 50 | $C_{22}H_{36}N_3O_{8.5}S$ | 51.75 | 7.11 | 8.23 | 51.88 | 7.05 | 8.46 |
| 51 | $C_{20}H_{29}N_3O_6Cl_2$ | 50.22 | 6.11 | 8.78 | 50.02 | 6.14 | 8.89 |
| 52 | $C_{23}H_{35}N_3O_6$ | 61.45 | 7.85 | 9.35 | 61.06 | 7.83 | 9.17 |
| 66 | $C_{20}H_{33}N_3O_6$ | 58.38 | 8.08 | 10.21 | 58.40 | 8.10 | 10.31 |
| 67 | $C_{25}H_{39}N_3O_{10}S$ | 52.34 | 6.85 | 7.33 | 51.95 | 7.13 | 7.57 |
| 68 | $C_{16}H_{26}N_4O_4$ | 56.79 | 7.74 | 16.56 | 56.47 | 7.74 | 16.56 |
| 69 | $C_{21}H_{33}N_3O_8S$ | 51.73 | 6.82 | 8.62 | 51.31 | 6.84 | 8.36 |
| 70 | $C_{20}H_{33}N_3O_{6.5}F$ | 54.78 | 7.59 | 9.58 | 54.48 | 7.39 | 9.87 |
| 71 | $C_{18}H_{28}N_3O_6F$ | 53.86 | 7.03 | 10.47 | 53.41 | 6.98 | 10.58 |
| 72 | $C_{12}H_{32}N_4O_6$ | 57.78 | 7.39 | 12.84 | 57.46 | 7.47 | 12.76 |

Pharmacology

The action of compounds of this invention in correcting cardiac arrhythmias or preventing cardiac arrhythmias is demonstrated by the following procedures:

Ouabain Induced Arrhythmias

Correction of existing cardiac arrhythmias of ventricular origin is carried out on (1) adult mongrel dogs which are under barbiturate anesthesia during the test. A Grass Model 7 polygraph was used for recording femoral arterial blood pressure (Statham P23AC transducer) and the electrocardiogram (Grass 7P4 preamplifier). Ouabain was given intravenously in an initial dose of 40 μg/kg and in a second dose of 20 μg/kg 30 minutes after the first dose and in subsequent doses of 10 μg/kg which were repeated at 15 min. intervals as required for producing cardiac arrhythmias that persisted for at least 15 minutes. When the arrhythmias were established, the test compounds were administered by infusion (Harvard Model 942 Infusion Pump) into a femoral vein at a rate of 1 mg/kg/min. Concentration of compound was adjusted according to the weight of the dog to allow a volume infusion of 1 ml/min. The compound was considered to be active as antiarrhythmic agent if reversion to to sinus rhythm occurred which was maintained for at least 30 min.

Coronary Artery Ligation Induced Arrhythmias

Adult mongrel dogs which are in the conscious state were used for the test and cardiac arrhythmias were induced by prior (22–24 hr) surgical preparation in which blood flow through a coronary artery was occluded by use of a constrictor device as reported by Smith et al, 1973. A Grass Model 79 polygraph was used for recording the electrocardiogram (Grass 7P4 preamplifier).

The test compound was administered by infusion (Howard Model 942 Infusion Pump) into a sapheneous vein to one group of dogs at a rate of 0.5 mg/kg/min. Concentration of compound was adjusted according to the weight of the dog to allow a volume of infusion of 0.5 ml/min. The test compound was administered orally by gavage to another group of dogs at dose levels of 10 through 40 mg/kg. The test compound was prepared in distilled water to give a total volume of 20 ml. Following the administration of the test compound, the heart rate number of ectopic cardiac beats per min. and the percent ectopic beats (Ectopic beats/HR X100) were recorded at 15 min. intervals. The compound was considered active if it abolished the ectopic ventricular frequency and caused a return to normal sinus rhythm within 2 hours of administration.

Injury-Stimulus Induced Arrhythmias

Correction of existing arrhythmias of atrial origin is carried out on adult mongrel dogs which are under barbiturate anesthesia and mechanical respiration (Harvard Respiration Pump Model 6B). During the test a Grass Model 7 polygraph was used for recording femoral arterial blood pressure (Statham P23AC Transducer) and the electrocardiogram (Grass 7p4 preamplifier). The heart was exposed by an incision at the fourth intercostal space space of the right thorax and the right atrium was exposed. A band of right atrial tissue lying betweeen the superior and inferior vena cava was crushed using hemostatic forceps. Atrial arrhythmias were initiated by applying an electrical stimulus of 1 m sec, 20–100 Hz and 3–5 V to the crushed area (Method of Rosenbluth & Garcia-Ramos). When the arrhythmias were established and persisted for at least 15 min., the test compound was administered by infusion (Harvard Model 940 Infusion Pump) into a femoral vein at a rate of 1 mg/kg/min. Concentration of the test compound was adjusted according to the weight of the dog to allow a volume infusion of 1 ml/min. The compound was considered active as an anti-arrhythmic agent if the induced arrhythmia (atrial flutter or atrial fibrillation) was reverted to a normal sinus rhythm and the atrial frequency is diminished in order that a 1:1 relationship of atrial and ventricular was established.

Acetylcholine Induced Arrhythmias

Protection activity against the induction of cardiac arrhythmias of atrial origin were carried out in adult mongrel dogs which were under barbiturate anesthesia and mechanical respiration (Harvard Respiration Pump Model 613). A Grass Model 7 Polygraph was used for recording femoral arterial blood pressure (P23Ac Transducer) and the electrocardiogram. The heart was exposed by an incision at the fourth intercostal space of the right thorax and the right atrium was exposed. An atrial arrhythmia was produced by placing 2 drops of a 10% aqueous solution of acetylcholine directly on the right atrium and stroking the area of application with a cotton applicator (Method of Scherf & Chick). The time period of the arrhythmia was determined by noting the spontaneous return of the sinus rhythm of the electrocardiogram. This procedure was repeated at 15 min. intervals until at least 2 consecutive periods of arrhythmia of comparable duration were obtained.

The test compound was administered intravenously as an aqueous solution at an initial dose of 1 mg active compound per kilogram of body weight. After drug administration, attempts were made up to 60 min. to reproduce the arrhythmia. Higher dosages of the test compound were administered if lower levels failed to prevent the occurrence of the arrhythmia during the 60 min. trial period.

Data obtained for one preferred compound; namely, N-[2-(3,5-dichlorophenoxy)ethyl]-N'-[2-(dimethylamino)ethyl]-N-(1-methylethyl)urea as represented by its maleate salt of Example 3 are shown in Table 3. This compound exhibited minimal CNS side effects as compared to quinidine and lidocaine. The other compounds of this invention show qualitatively by similar effects in one or more types of arrhythmias as represented by the foregoing tests and generally exhibit less side effects than quinidine or lidocaine.

TABLE 3

Effect of Compounds on Cardiac Arrhythmias in Dogs

| Example No. | Ouabain[1][5] Induced Correcting Dose Range mg/kg, I.V. | Coronary Artery Ligation-Induced[2][5] Correcting Dose Range mg/kg, I.V. | Injury Stimulus-Induced[3][6] Correcting Dose Range mg/kg, I.V. | Acetyl Choline-Induced[4][6] Protecting Dose Range, mg/kg, I.V. |
|---|---|---|---|---|
| 2 | 4–9 | 4–7 | no data | no data |
| 3 | 3–15 | 3–15 | 10–40 | 1–8 |
| 13 | 3–6 | 3–9 | no data | no data |
| 20 | 3–6 | 5–8 | " | " |
| 21 | 6–15 | 2–8 | " | " |
| 27 | 7–9 | 4–8 | " | " |
| 31 | 4–8 | 2–6 | " | " |
| 48 | no data | 1–4 | " | " |
| 50 | no data | 3–5 | " | " |

[1]Cardiac arrhythmias produced by Method of Lucchessi and Hardman, 1961, U. Pharmacol. Exp. Ther., 132, 373–381.
[2]Cardiac arrhythmias produced by modification of Method of Harris, 1950, Circulation 1, 1318, as reported by Smith et al, 1973, Pharmacologist 15, 192.
[3]Cardiac arrhythmias produced by Method of Rosenblueth and Garcia-Ramos, 1947, Am. Heart. J. 33, 677.
[4]Cardiac arrhythmias produced by Method of Scherf and Chick, 1951, Circulation 3, 764.
[5]Cardiac arrhythmia of ventricular origin.
[6]Cardiac arrhythmia of atrial origin.

Pharmaceutical Compositions

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid; e.g., water, or a parenterally acceptable oil; e.g., arachis oil, contained in ampoules.

In compositions for rectal administration the carrier can comprise a suppository base; e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on aminals suggests the the oral dosage effective to correct arrhythmias will be about 3 times that of the intravenous dosage. The animal data also suggest dosage requirements will be about half that of quinidine for the more active compounds.

Based on the animal data, allowing for variation in species and severity of cardiac arrhythmia unit dosages containing an amount of compound equivalent to about 1 to about 100 mg/kg of body weight, are contemplated. Based on all of the above considerations, a choice in a range of unit oral dosages for humans of about 10 to about 1000 mg is contemplated, preferably about 10 to 600 mg for a more active compound such as Example 3. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

| Capsules | |
|---|---|
| Ingredients | Per Cap. |
| 1. Active ingredient | 10.0 mg. |
| 2. Lactose | 146.0 mg. |
| 3. Magnesium Stearate | 4.0 mg. |

Procedure
1. Blend 1, 2, and 3.
2. Mill this blend and blend again.
3. This milled blend is then filled into #1 hard gelatin capsules.

| Tablets (10 mg) | |
|---|---|
| Ingredients | Mg./Tab. |
| 1. Active ingredient | 10.0 mg. |
| 2. Corn starch | 20.0 mg. |
| 3. Kelacid | 20.0 mg. |
| 4. Keltose | 20.0 mg. |

-continued

| 5. Magnesium stearate | 1.3 mg. |
|---|---|
| Tablets (50 mg) | |
| Ingredients | Mg/Tab. |
| 1. Active ingredient | 50.0 mg. |
| 2. Milo starch | 20.0 mg. |
| 3. Corn starch | 38.0 mg. |
| 4. Lactose | 90.0 mg. |
| 5. Calcium stearate | 2.0 mg. |
| | 200.0 mg. |

Procedure
1. Blend 1, 2 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg. |
| 2. pH 4.0 Buffer solution | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml. |
| 1. Active ingredients | 5.0 mg. |
| 2. Isotonic Buffer solution 4.0 | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredients | Per Supp. |
| 1. Active ingredient | 10.0 Img. |
| 2. Polyethylene Glycol 1000 | 1350.0 mg. |
| 3. Polyethylene Glycol 4000 | 450.0 mg. |

Procedure
1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

Therapeutic compositions having cardiac arrhythmia inhibiting activity in dosage unit form, comprising a pharmaceutical carrier and a cardiac arrhythmia inhibiting amount of a compound of Formula I or a pharmaceutically acceptable acid addition salt thereof are therefore an embodiment of this invention.

Various modifications and equivalents will be apparent to one skilled in the art and may be made in the compounds, method, and compositions of the present invention without departing from the spirit or scope thereof, and it is therefore to be understood that the invention is to be limited only by the scope of the appended claims.

What is claimed is:

1. A method for treating cardiac arrhythmia in an animal which comprises administering to said animal an effective amount of a compound having the formula:

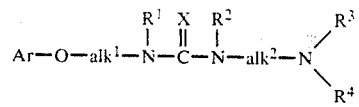

wherein;

Ar is 1 and 2-naphthyl, 2,3-dihydro-1H-inden-4(or 5)yl, 3-pyridinyl, phenyl or phenyl substituted by 1–3 radicals which may be the same or different selected from the group consisting of loweralkyl, loweralkoxy, halogen, trifluoromethyl, amino, cyano, aminocarbonyl, nitro, loweralkylthio, loweralkylsulfinyl, loweralkylsulfonyl, loweralkanoyl, benzoylamino or loweralkanoylamino;

$R^1$ and $R^2$ are selected from the group consisting of hydrogen, loweralkyl, cycloalkyl containing 3 to 9 carbon atoms, phenyl, phenyl substituted by halogen, loweralkyl or loweralkoxy, or phenyl-loweralkyl wherein phenyl may also be substituted by halogen, loweralkyl or loweralkoxy;

X is selected from oxygen or sulfur;

$R^3$ and $R^4$ are selected from the group consisting of hydrogen, loweralkyl, phenyl and phenyl-loweralkyl and may be the same or different or $R^3$ and $R^4$ taken together with the adjacent nitrogen form a heterocyclic residue selected from the group consisting of pyrrolidino, piperidino, 4-phenylpiperidino, 2,6-loweralkyl-piperidino, 4-hydroxy-4-phenylpiperidino, 4-cyano-4-phenylpiperidino, 4-phenyl-1,2,3,6-tetrahydropyridino, piperazino, 4-loweralkylpiperazino, 4-phenyl-piperazino, 4-phenylloweralkylpiperazino or morpholino radicals;

$alk^1$ and $alk^2$ are selected from the group consisting of loweralkylene or loweralkylene-loweralkyl and may be the same or different, or a pharmaceutically acceptable addition salt or hydrate thereof.

2. The method of claim 1 wherein the compound is N-[2-(3,4-dichlorophenoxy)ethyl]-N'-[2-dimethylamino)ethyl]-N-(1-methylethyl)urea, or a pharmaceutically acceptable addition salt or hydrate thereof.

3. The method of claim 1 wherein the compound is N-[2-(3,5-dichlorophenoxy)ethyl]-N'-[2-(dimethylamino)ethyl]-N-(1-methylethyl)urea, or a pharmaceutically acceptable addition salt or hydrate thereof.

4. The method of claim 1 wherein the compound is N-[2-(3,4-dichlorophenoxy)ethyl]-N'-[3-(dimethylamino)propyl]-N-(1-methylethyl)urea, or a pharmaceutically acceptable addition salt or hydrate thereof.

5. The method of claim 1 wherein the compound is N-[3-(3,5-dichlorophenoxy)propyl]-N'-[2-(dimethylamino)ethyl]N-(1-methylethyl)urea, or a pharmaceutically acceptable addition salt or hydrate thereof.

6. The method of claim 1 wherein the compound is N'-[2-(dimethylamino)ethyl]-N-(1-methylethyl)-N-(2-phenoxyethyl)urea, or a pharmaceutically acceptable addition salt or hydrate thereof.

7. The method of claim 1 wherein the compound is N-[3-(3,5-dichlorophenoxy)propyl]-N'-[3-(dimethylamino)propyl]-N-(1-methylethyl)urea, or a pharmaceutically acceptable addition salt or hydrate thereof.

8. The method of claim 1 wherein the compound is N-[2-(3,5-dichlorophenoxy)ethyl]-N'-[3-dimethylamino)propyl]-N-(1-methylethyl)urea, or a pharmaceutically acceptable addition salt or hydrate thereof.

9. The method of claim 1 wherein the compound is N-[2-(3,5-dichlorophenoxy)ethyl]-N-(1-methylethyl)-N'-[2-[bis(1-methylethyl)amino]ethyl]urea, or a pharmaceutically acceptable addition salt or hydrate thereof.

10. The method of claim 1 wherein the compound is N'-[2-(dimethylamino)ethyl]-N-[2-(3,4-dimethylphenoxy)ethyl]-N-(1-methylethyl)urea, or a pharmaceutically acceptable addition salt or hydrate thereof.

11. The method of claim 1 wherein the compound is N-[2-(2,4-dichlorophenoxy)ethyl]-N'-[2-(dimethylamino)ethyl]-N-(1-methylethyl)urea, or a pharmaceutically acceptable addition salt or hydrate thereof.

12. The method of claim 1 wherein the compound is N-[2-(3,5-dichlorophenoxy)ethyl]-N'-[2-(dimethylamino)ethyl]-N-phenylurea, or a pharmaceutically acceptable addition salt or hydrate thereof.

13. The method of claim 1 wherein the compound is N'-[2-(dimethylamino)ethyl]-N-(1-methylethyl)-N-[2-(1-naphthalenyloxy)ethyl]urea, or a pharmaceutically acceptable addition salt or hydrate thereof.

14. The method of claim 1 wherein the compound is N-[2-(3-chlorophenoxy)ethyl]-N'-[2-dimethylamino)ethyl]-N-(1-methylethyl)urea, or a pharmaceutically acceptable addition salt or hydrate thereof.

15. The method of claim 1 wherein the compound is N-[2-(2,6-dichlorophenoxy)ethyl]-N'-[2-(dimethylamino)ethyl]-N-(1-methylethyl)urea, or a pharmaceutically acceptable addition salt or hydrate thereof.

16. The method of claim 1 wherein the compound is N-[2-(3,5-dichlorophenoxy)ethyl]-N'-[2-dimethylamino)ethyl]-N'-methyl-N-(1-methylethyl)urea, or a pharmaceutically acceptable addition salt or hydrate thereof.

17. The method of claim 1 wherein the compound is N-[2-(3,5-dichlorophenoxy)ethyl]-N'-[2-(dimethylamino)ethyl]urea, or a pharmaceutically acceptable addition salt or hydrate thereof.

18. The method of claim 1 wherein the compound is N'[2-(dimethylamino)ethyl]-N-[2-(3,5-dimethylphenoxy)ethyl]-N-(1-methylethyl)urea, or a pharmaceutically acceptable addition salt or hydrate thereof.

19. The method of claim 1 wherein the compound is N-[2-(3,5-dimethoxyphenoxy)ethyl]-N'-[2-(dimethylamino)ethyl]-N-(1-methylethyl)urea, or a pharmaceutically acceptable addition salt or hydrate thereof.

20. The method of claim 1 wherein the compound is N'-[2-(dimethylamino)ethyl]-N-[2-(3,4-dimethylphenoxy)ethyl]-N-(1-methylethyl)urea, or a pharmaceutically acceptable addition salt or hydrate thereof.

21. The method of claim 1 wherein the compound is N-[2-(3-chlorophenoxy)ethyl]-N'-[2-(dimethylamino)ethyl]-N-(1-methylethyl)urea, or a pharmaceutically acceptable addition salt or hydrate thereof.

22. The method of claim 1 wherein the compound is N-[2-(2,5-dichlorophenoxyethyl]-N'-[2-(dimethylamino)ethyl]-N-(1-methylethyl)urea, or a pharmaceutically acceptable addition salt or hydrate thereof.

23. The method of claim 1 wherein the compound is N-[2-(3,5-dichlorophenoxy)ethyl]-N-(1-methylethyl)-N'-[2-(4-morpholinyl)ethyl]urea, or a pharmaceutically acceptable addition salt or hydrate thereof.

24. The method of claim 1 wherein the compound is N'-[2-(dimethylamino)ethyl]-N-(1-methylethyl)-N-[2-(3-trifluoromethylphenoxy)ethyl]urea, or a pharmaceutically acceptable addition salt or hydrate thereof.

25. The method of claim 1 wherein the compound is N-[2-(3,5-dichlorophenoxy)ethyl]-N'-[2-(dimethylamino)ethyl]-N-methyl urea, or a pharmaceutically acceptable addition salt or hydrate thereof.

26. The method of claim 1 wherein the compound is N'-[2-(dimethylamino)ethyl]-N-[2-(3-fluorophenoxy)ethyl]-N-(1-methylethyl)urea, or a pharmaceutically acceptable addition salt or hydrate thereof.

27. The method of claim 1 wherein the compound is N-[2-(2,3-dichlorophenoxy)ethyl]-N'-[2-(dimethylamino)ethyl]-N-(1-methylethyl)urea, or a pharmaceutically acceptable addition salt or hydrate thereof.

28. The method of claim 1 wherein the compound is N-[2-(2-chlorophenoxy)ethyl]-N'-[2-(dimethylamino)ethyl]-N-(1-methylethyl)urea, or a pharmaceutically acceptable addition salt or hydrate thereof.

29. The method of claim 1 wherein the compound is N'-[2-(dimethylamino)ethyl]-N-(1-methylethyl)-N-[2-(2-naphthalenyloxy)ethyl]urea, or a pharmaceutically acceptable addition salt or hydrate thereof.

30. The method of claim 1 wherein the compound is N'-[2-(dimethylamino)ethyl]-N-[2-[(2,3-dihydro-1H-inden-5-yl)oxy]ethyl]-N-(1-methylethyl)urea, or a pharmaceutically acceptable addition salt or hydrate thereof.

31. The method of claim 1 wherein the compound is N'-[2-(dimethylamino)ethyl]-N-[2-[(2,3-dihydro-1H-inden-4-yl)oxy]ethyl]-N-(1-methylethyl)urea, or a pharmaceutically acceptable addition salt or hydrate thereof.

32. The method of claim 1 wherein the compound is N-[2-(3,5-dichlorophenoxy)ethyl]-N'-methyl-N'-[2-(methylamino)ethyl]-N-(1-methylethyl)urea, or a pharmaceutically acceptable addition salt or hydrate thereof.

33. The method of claim 1 wherein the compound is N'-[2-[(2,3-dihydro-1H-inden-4-yl)oxy]ethyl]-N-[2-(methylamino)ethyl]-N-methylurea, or a pharmaceutically acceptable addition salt or hydrate thereof.

34. The method of claim 1 wherein the compound is N-n-butyl-N-[2-(3,5-dichlorophenoxy)ethyl]-N'-[2-(dimethylamino)ethyl]urea, or a pharmaceutically acceptable addition salt or hydrate thereof.

35. The method of claim 1 wherein the compound is N-[2-(3,5-dichlorophenoxy]ethyl]-N'-[2-(dimethylamino)ethyl]-N-propylurea, or a pharmaceutically acceptable addition salt or hydrate thereof.

36. The method of claim 1 wherein the compound is N-cyclohexyl-N-[2-(3,5-dichlorophenoxy)ethyl]-N'-[2-(dimethylamino)ethyl]urea, or a pharmaceutically acceptable addition salt or hydrate thereof.

37. The method of claim 1 wherein the compound is N-[2-(3,5-dichlorophenoxy)ethyl]-N'-[2-(dimethylamino)ethyl]-N-(2-methylpropyl)urea, or a pharmaceutically acceptable addition salt or hydrate thereof.

38. The method of claim 1 wherein the compound is N'-[2-(3,5-dichlorophenoxy)ethyl]-N-[2-(dimethylamino)ethyl]-N-methylurea, or a pharmaceutically acceptable addition salt or hydrate thereof.

39. The method of claim 1 wherein the compound is N-[2-(3,5-dichlorophenoxy)ethyl]-N-(1-methylethyl)-N'-(2-aminoethyl)urea, or a pharmaceutically acceptable addition salt or hydrate thereof.

40. The method of claim 1 wherein the compound is N'-[2-(diethylamino)ethyl]-N-methyl-N-(2-phenoxyethyl)urea, or a pharmaceutically acceptable addition salt or hydrate thereof.

41. The method of claim 1 wherein the compound is N-methyl-N-(2-phenoxyethyl)-N'-[2-(1-pyrrolidinyl)ethyl]urea, or a pharmaceutically acceptable addition salt or hydrate thereof.

42. The method of claim 1 wherein the compound is N-[2-(3,5-dichlorophenoxy)ethyl]-N'-[2-(diethylamino)ethyl]-N-(1-methylethyl)urea, or a pharmaceutically acceptable addition salt or hydrate thereof.

43. The method of claim 1 wherein the compound is N-[2-(3,5-dichlorophenoxy)ethyl]-N'-[2-(dimethylamino)ethyl]-N-(1-methylethyl)thiourea, or a pharmaceutically acceptable addition salt or hydrate thereof.

44. The method of claim 1 wherein the compound is N'-[2-(diethylamino)ethyl]-N-(1-methylethyl)-N-(2-phenoxyethyl)thiourea, or a pharmaceutically acceptable addition salt or hydrate thereof.

45. The method of claim 1 wherein the compound is N'-[2-(dimethylamino)ethyl]-N-(1-methylethyl)-N-[2-(1-naphthalenyloxy)ethyl]thiourea, or a pharmaceutically acceptable addition salt or hydrate thereof.

46. The method of claim 1 wherein the compound is N'-[2-(dimethylamino)ethyl]-N-methyl-N-(2-phenoxyethyl)thiourea, or a pharmaceutically acceptable addition salt or hydrate thereof.

47. The method of claim 1 wherein the compound is N'-[2-[(3,5-dichlorophenyl)oxy]ethyl]-N-[2-(dimethylamino)ethyl]-N-(1-methylethyl)urea, or a pharmaceutically acceptable addition salt or hydrate thereof.

48. The method of claim 1 wherein the compound is N'-[2-[2,3-dihydro-1H-inden-4-yl)oxy]ethyl]-N-[2-(dimethylamino]ethyl]-N-(1-methylethyl)urea, or a pharmaceutically acceptable addition salt thereof.

49. The method of claim 1 wherein the compound is N'-[2-(dimethylamino)ethyl]-N-[2-(2,6-dimethylphenoxy)ethyl]-N-(1-methylethyl)urea, or a pharmaceutically acceptable addition salt or hydrate thereof.

50. The method of claim 1 wherein the compound is N'-[2-(diethylamino)ethyl]-N-(1-methylethyl)-N-[2-[4-(methylsulfonyl)phenoxy]ethyl]urea, or a pharmaceutically acceptable addition salt or hydrate thereof.

51. The method of claim 1 wherein the compound is N'-[2-(dimethylamino)ethyl]-N-(1-methylethyl)-N-[2-(4-nitrophenoxy)ethyl]urea, or a pharmaceutically acceptable addition salt or hydrate thereof.

52. The method of claim 1 wherein the compound is N'-[2-(dimethylamino)ethyl]-N-(1-methylethyl)-N-[2-[4-(methylsulfonyl)phenoxy]ethyl]urea, or a pharmaceutically acceptable addition salt or hydrate thereof.

53. The method of claim 1 wherein the compound is N'-[2-(diethylamino)ethyl]-N-[2-(4-fluorophenoxy)ethyl]-N-(1-methylethyl)urea, or a pharmaceutically acceptable addition salt or hydrate thereof.

54. The method of claim 1 wherein the compound is N'-[2-(dimethylamino)ethyl]-N-[2-(4-fluorophenoxy)ethyl]-N-(1-methylethyl)urea, or a pharmaceutically acceptable addition salt or hydrate thereof.

55. The method of claim 1 wherein the compound is N-[2-(2-cyanophenoxy)ethyl]-N'-[2-(diethylamino)ethyl]-N-(1-methylethyl)urea, or a pharmaceutically acceptable addition salt or hydrate thereof.

56. The method of claim 1 wherein the compound is N'-[2-(diethylamino)ethyl]-N-methyl-N-(2-phenoxyethyl)thiourea or a pharmaceutically acceptable addition salt or hydrate thereof.

57. A therapeutic composition having cardiac arrhythmic inhibiting activity comprising (a) an effective amount of a compound selected from N-[2-(3,5-dichlorophenoxy)ethyl]-N'-[2-(dimethylamino)ethyl]-N-(1-methylethyl)urea, or a pharmaceutically acceptable addition salt or hydrate thereof, and (b) a pharmaceutical carrier therefor.

58. A composition of claim 57 wherein the compound is N-[2-(3,5-dichlorophenoxy)ethyl]-N'-[2-dimethylamino)ethyl]-N-(1-methylethyl)urea, or a pharmaceutically acceptable addition salt or hydrate thereof.

59. A therapeutic composition having cardiac arrhythmic inhibiting activity comprising (a) an effective amount of a compound selected from N-[2-(3,4-dichlorophenoxy)ethyl]-N'-[2-(dimethylamino)ethyl]-(1-methylethyl)urea or a pharmaceutically acceptable addition salt or hydrate thereof, and (b) a pharmaceutical carrier therefor.

60. A therapeutic composition having cardiac arrhythmic inhibiting activity comprising (a) an effective amount of a compound selected from N'-[2-(dimethylamino)ethyl]-N-(1-methylethyl)-N-[2-(1-naphthyleneoxy)ethyl]urea or a pharmaceutically acceptable addition salt or hydrate thereof, and (b) a pharmaceutical carrier therefor.

61. A therapeutic composition having cardiac arrhythmic inhibiting activity comprising (a) an effective amount of a compound selected from N'-[2-(dimethylamino)ethyl]-N-[2-(3,4-dimethylphenoxy)ethyl]-N-(1-methylethyl)urea, or a pharmaceutically acceptable addition salt or hydrate thereof, and (b) a pharmaceutical carrier therefor.

62. A therapeutic composition having cardiac arrhythmic inhibiting activity comprising (a) an effective amount of a compound selected from N-[2-(4-chlorophenoxy)ethyl]-N'-[2-(dimethylamino)ethyl]-N-(1-methylethyl)urea, or a pharmaceutically acceptable addition salt or hydrate thereof, and (b) a pharmaceutical carrier therefor.

63. A therapeutic composition having cardiac arrhythmic inhibiting activity comprising (a) an effective amount of a compound selected from N-[2-(2,3-dichlorophenoxy)ethyl]-N'-[2-(dimethylamino)ethyl]-N-(1-methylethyl)urea, or a pharmaceutically acceptable addition salt or hydrate thereof, and (b) a pharmaceutical carrier therefor.

64. A therapeutic composition having a cardiac arrhythmic inhibiting activity comprising (a) an effective amount of a compound selected from N'-[2-(dimethylamino)ethyl]-N-[2-(2,3-dihydro-1H-inden-4-yl)oxy]ethyl]-N-(1-methylethyl)urea or a pharmaceutically acceptable addition salt or hydrate thereof, and (b) a pharmaceutical carrier therefor.

65. A therapeutic composition having a cardiac arrhythmic inhibiting activity comprising (a) an effective amount of a compound selected from N'-[2-(diethylamino)ethyl]-N-(1-methylethyl)-N-(2-phenoxyethyl)thiourea, or a pharmaceutically acceptable addition salt or hydrate thereof, and (b) a pharmaceutical carrier therefor.

* * * * *